(12) United States Patent
Litscher et al.

(10) Patent No.: US 7,597,662 B2
(45) Date of Patent: Oct. 6, 2009

(54) MULTI-FLUID DELIVERY SYSTEM

(75) Inventors: Eric Litscher, Hopkinton, MA (US);
Gerald Heller, Bedford, MA (US);
Daniel Macari, Somerville, MA (US);
Charles McCall, Plymouth, MA (US);
Eric Rioux, Quincy, MA (US); Gary Searle, Norfolk, MA (US); Arthur Stephen, Raynham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 254 days.

(21) Appl. No.: 11/430,518

(22) Filed: May 8, 2006

(65) Prior Publication Data

US 2006/0276689 A1 Dec. 7, 2006

Related U.S. Application Data

(63) Continuation-in-part of application No. 11/239,644, filed on Sep. 29, 2005.

(60) Provisional application No. 60/614,868, filed on Sep. 30, 2004.

(51) Int. Cl.
*A61B 1/12* (2006.01)
*A61B 1/04* (2006.01)

(52) U.S. Cl. ...................... 600/159; 600/118

(58) Field of Classification Search ............... 600/118, 600/126, 152, 159, 132; 604/30; 348/72, 348/75
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 3,638,013 A * | 1/1972 | Keller | 433/31 |
| 4,108,211 A | 8/1978 | Tanaka | |
| 4,256,442 A * | 3/1981 | Lamadrid et al. | 417/477.11 |
| 4,286,585 A | 9/1981 | Ogawa | |
| 4,294,162 A | 10/1981 | Fowler et al. | |
| 4,311,134 A | 1/1982 | Mitsui et al. | |

(Continued)

FOREIGN PATENT DOCUMENTS

EP 0 075 153 B1 3/1983

(Continued)

OTHER PUBLICATIONS

Office Action dated Oct. 30, 2008, from U.S. Appl. No. 11/239,644, filed Sep. 29, 2005, of which the present application is a continuation-in-part.

*Primary Examiner*—Linda C Dvorak
*Assistant Examiner*—Alireza Nia
(74) *Attorney, Agent, or Firm*—Christensen O'Connor Johnson Kindness PLLC

(57) ABSTRACT

A proximal connector of an endoscope shaft can be manually attached to and detached from a console, such that the connector and endoscope shaft can be provided as a single use device. An interface between the proximal connector and console can include a sliding plate moveable to operably make and break at least some of the connections between the console and endoscope shaft. A fluid reservoir may be separately connected to the proximal connector and hang from a mount on the interface.

10 Claims, 33 Drawing Sheets

U.S. PATENT DOCUMENTS

| | | |
|---|---|---|
| 4,315,309 A | 2/1982 | Coli |
| 4,351,323 A | 9/1982 | Ouchi et al. |
| 4,402,310 A | 9/1983 | Kimura |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,493,537 A | 1/1985 | Nakahashi |
| 4,495,134 A | 1/1985 | Ouchi et al. |
| 4,499,895 A | 2/1985 | Takayama |
| 4,503,842 A | 3/1985 | Takayama |
| 4,513,235 A | 4/1985 | Acklam et al. |
| 4,515,444 A | 5/1985 | Prescott et al. |
| 4,516,063 A | 5/1985 | Kaye et al. |
| 4,519,391 A | 5/1985 | Murakoshi |
| 4,552,130 A | 11/1985 | Kinoshita |
| 4,559,928 A | 12/1985 | Takayama |
| 4,566,437 A | 1/1986 | Yamaguchi |
| 4,573,450 A | 3/1986 | Arakawa |
| 4,580,210 A | 4/1986 | Nordstrom |
| 4,586,923 A | 5/1986 | Gould et al. |
| 4,615,330 A | 10/1986 | Nagasaki et al. |
| 4,616,630 A | 10/1986 | Arakawa |
| 4,617,915 A | 10/1986 | Arakawa |
| 4,618,884 A | 10/1986 | Nagasaki |
| 4,621,618 A | 11/1986 | Omagari et al. |
| 4,622,584 A | 11/1986 | Nagasaki et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okobe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,798,590 A * | 1/1989 | O'Leary et al. ............. 604/153 |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,844,071 A | 7/1989 | Chen et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,897,789 A | 1/1990 | King et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,044,063 A * | 9/1991 | Voellmer ................... 483/59 |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,074,861 A | 12/1991 | Schneider et al. |
| 5,081,524 A | 1/1992 | Tsuruoka et al. |

| | | | | | | | |
|---|---|---|---|---|---|---|---|
| 5,087,989 | A | 2/1992 | Igarashi | 5,643,203 | A | 7/1997 | Beiser et al. |
| 5,110,645 | A | 5/1992 | Matsumoto et al. | 5,645,075 | A | 7/1997 | Palmer et al. |
| 5,111,281 | A | 5/1992 | Sekiguchi | 5,647,840 | A | 7/1997 | D'Amelio et al. |
| 5,111,306 | A | 5/1992 | Kanno et al. | 5,658,238 | A | 8/1997 | Suzuki et al. |
| 5,111,804 | A | 5/1992 | Funakoshi | 5,667,477 | A | 9/1997 | Segawa |
| 5,113,254 | A | 5/1992 | Kanno et al. | 5,674,182 | A | 10/1997 | Suzuki et al. |
| 5,119,238 | A | 6/1992 | Igarashi | 5,674,197 | A | 10/1997 | van Muiden et al. |
| 5,131,393 | A | 7/1992 | Ishiguro et al. | 5,682,199 | A * | 10/1997 | Lankford ............ 348/72 |
| 5,137,013 | A | 8/1992 | Chiba et al. | 5,685,823 | A | 11/1997 | Ito et al. |
| 5,140,265 | A | 8/1992 | Sakiyama et al. | 5,685,825 | A | 11/1997 | Takase et al. |
| 5,159,446 | A | 10/1992 | Hibino et al. | 5,691,853 | A | 11/1997 | Miyano |
| 5,163,900 | A * | 11/1992 | Wortrich ............ 604/30 | 5,695,450 | A | 12/1997 | Yabe et al. |
| 5,170,775 | A | 12/1992 | Tagami | 5,698,866 | A | 12/1997 | Doiron et al. |
| 5,172,225 | A | 12/1992 | Takahashi et al. | 5,701,155 | A | 12/1997 | Wood |
| 5,174,293 | A | 12/1992 | Hagiwara | 5,702,349 | A | 12/1997 | Morizumi |
| 5,176,629 | A | 1/1993 | Kullas et al. | 5,702,754 | A | 12/1997 | Zhong |
| 5,191,878 | A | 3/1993 | Iida et al. | 5,703,724 | A | 12/1997 | Miyano |
| 5,198,931 | A | 3/1993 | Igarashi | 5,704,371 | A | 1/1998 | Shepard |
| 5,201,908 | A | 4/1993 | Jones | 5,704,896 | A | 1/1998 | Fukunishi et al. |
| 5,208,702 | A | 5/1993 | Shiraiwa | 5,708,482 | A | 1/1998 | Takahashi et al. |
| 5,209,220 | A | 5/1993 | Hiyama et al. | 5,721,566 | A | 2/1998 | Rosenberg et al. |
| 5,225,958 | A | 7/1993 | Nakamura | 5,724,068 | A | 3/1998 | Sanchez et al. |
| 5,228,356 | A | 7/1993 | Chuang | 5,728,045 | A | 3/1998 | Komi |
| 5,243,416 | A | 9/1993 | Nakazawa | 5,739,811 | A | 4/1998 | Rosenberg et al. |
| 5,243,967 | A | 9/1993 | Hibino | 5,740,801 | A | 4/1998 | Branson |
| 5,257,628 | A | 11/1993 | Ishiguro et al. | 5,746,696 | A | 5/1998 | Kondo |
| 5,271,381 | A | 12/1993 | Ailinger et al. | 5,764,809 | A | 6/1998 | Nomami et al. |
| RE34,504 | E | 1/1994 | Uehara et al. | 5,767,839 | A | 6/1998 | Rosenberg |
| 5,291,010 | A | 3/1994 | Tsuji | 5,779,686 | A | 7/1998 | Sato et al. |
| 5,299,559 | A | 4/1994 | Bruce et al. | 5,781,172 | A | 7/1998 | Engel et al. |
| 5,311,858 | A | 5/1994 | Adair | 5,788,714 | A | 8/1998 | Ouchi |
| 5,325,845 | A | 7/1994 | Adair et al. | 5,789,047 | A | 8/1998 | Sasaki et al. |
| 5,331,551 | A | 7/1994 | Tsuruoka et al. | 5,793,539 | A | 8/1998 | Konno et al. |
| 5,342,299 | A | 8/1994 | Snoke et al. | 5,805,140 | A | 9/1998 | Rosenberg et al. |
| 5,347,989 | A | 9/1994 | Monroe et al. | 5,810,715 | A | 9/1998 | Moriyama |
| 5,374,953 | A | 12/1994 | Sasaki et al. | 5,812,983 | A | 9/1998 | Kumagai |
| 5,379,757 | A | 1/1995 | Hiyama et al. | 5,819,736 | A | 10/1998 | Avny et al. |
| 5,381,782 | A | 1/1995 | DeLaRama et al. | 5,820,591 | A | 10/1998 | Thompson et al. |
| 5,390,662 | A | 2/1995 | Okada | 5,821,466 | A | 10/1998 | Clark et al. |
| 5,400,769 | A | 3/1995 | Tanii et al. | 5,821,920 | A | 10/1998 | Rosenberg et al. |
| 5,402,768 | A | 4/1995 | Adair | 5,823,948 | A | 10/1998 | Ross, Jr. et al. |
| 5,402,769 | A | 4/1995 | Tsuji | 5,827,186 | A | 10/1998 | Chen et al. |
| 5,409,485 | A | 4/1995 | Suda | 5,827,190 | A | 10/1998 | Palcic et al. |
| 5,412,478 | A | 5/1995 | Ishihara et al. | 5,828,197 | A | 10/1998 | Martin et al. |
| 5,418,649 | A | 5/1995 | Igarashi | 5,828,363 | A | 10/1998 | Yaniger et al. |
| 5,420,644 | A | 5/1995 | Watanabe | 5,830,124 | A | 11/1998 | Suzuki et al. |
| 5,431,645 | A | 7/1995 | Smith et al. | 5,830,128 | A | 11/1998 | Tanaka |
| 5,434,615 | A | 7/1995 | Matsumoto | 5,833,935 | A | 11/1998 | Malchesky |
| 5,436,640 | A | 7/1995 | Reeves | 5,836,869 | A | 11/1998 | Kudo et al. |
| 5,436,767 | A | 7/1995 | Suzuki et al. | 5,837,023 | A | 11/1998 | Koike et al. |
| 5,440,341 | A | 8/1995 | Suzuki et al. | 5,840,014 | A | 11/1998 | Miyano et al. |
| 5,464,007 | A | 11/1995 | Krauter et al. | 5,841,126 | A | 11/1998 | Fossum et al. |
| 5,469,840 | A | 11/1995 | Tanii et al. | 5,843,000 | A | 12/1998 | Nishioka et al. |
| 5,473,235 | A | 12/1995 | Lance et al. | 5,846,183 | A | 12/1998 | Chilcoat |
| 5,482,029 | A | 1/1996 | Sekiguchi et al. | 5,855,560 | A | 1/1999 | Idaomi et al. |
| 5,484,407 | A | 1/1996 | Osypka | 5,857,963 | A | 1/1999 | Pelchy et al. |
| 5,485,316 | A | 1/1996 | Mori et al. | 5,865,724 | A | 2/1999 | Palmer et al. |
| 5,496,260 | A | 3/1996 | Krauter et al. | 5,868,664 | A | 2/1999 | Speier et al. |
| 5,515,449 | A | 5/1996 | Tsuruoka et al. | 5,868,666 | A | 2/1999 | Okada et al. |
| 5,518,501 | A | 5/1996 | Oneda et al. | 5,873,816 | A | 2/1999 | Kagawa et al. |
| 5,518,502 | A | 5/1996 | Kaplan et al. | 5,873,866 | A | 2/1999 | Kondo et al. |
| 5,543,831 | A | 8/1996 | Tsuji et al. | 5,876,326 | A | 3/1999 | Takamura et al. |
| 5,569,158 | A | 10/1996 | Suzuki et al. | 5,876,331 | A | 3/1999 | Wu et al. |
| 5,569,159 | A | 10/1996 | Anderson et al. | 5,876,373 | A | 3/1999 | Giba et al. |
| 5,586,262 | A | 12/1996 | Komatsu et al. | 5,876,427 | A | 3/1999 | Chen et al. |
| 5,589,854 | A | 12/1996 | Tsai | 5,877,819 | A | 3/1999 | Branson |
| 5,591,202 | A | 1/1997 | Slater et al. | 5,879,284 | A | 3/1999 | Tsujita |
| 5,605,545 | A | 2/1997 | Nowosielski | 5,880,714 | A | 3/1999 | Rosenberg et al. |
| 5,608,451 | A | 3/1997 | Konno et al. | 5,882,293 | A | 3/1999 | Ouchi |
| 5,619,380 | A | 4/1997 | Ogasawara et al. | 5,882,339 | A | 3/1999 | Beiser et al. |
| 5,622,528 | A | 4/1997 | Hamano et al. | 5,889,670 | A | 3/1999 | Schuler et al. |
| 5,631,695 | A | 5/1997 | Nakamura et al. | 5,889,672 | A | 3/1999 | Schuler et al. |
| 5,633,203 | A | 5/1997 | Adair | 5,892,630 | A | 4/1999 | Broome |

| | | | | | | |
|---|---|---|---|---|---|---|
| 5,895,350 | A | 4/1999 | Hori | 6,154,198 | A | 11/2000 | Rosenberg |
| 5,897,507 | A | 4/1999 | Kortenbach et al. | 6,154,248 | A | 11/2000 | Ozawa et al. |
| 5,897,525 | A | 4/1999 | Dey et al. | 6,155,988 | A | 12/2000 | Peters |
| 5,907,487 | A | 5/1999 | Rosenberg et al. | 6,181,481 | B1 | 1/2001 | Yamamoto et al. |
| 5,923,018 | A | 7/1999 | Kameda et al. | 6,184,922 | B1 | 2/2001 | Saito et al. |
| 5,928,136 | A | 7/1999 | Barry | 6,193,714 | B1 | 2/2001 | McGaffigan et al. |
| 5,929,607 | A | 7/1999 | Rosenberg et al. | 6,195,592 | B1 | 2/2001 | Schuler et al. |
| 5,929,846 | A | 7/1999 | Rosenberg et al. | 6,203,493 | B1 | 3/2001 | Ben-Haim |
| 5,929,900 | A | 7/1999 | Yamanaka | 6,206,824 | B1 | 3/2001 | Ohara et al. |
| 5,929,901 | A | 7/1999 | Adair et al. | 6,211,904 | B1 | 4/2001 | Adair |
| 5,931,833 | A | 8/1999 | Silverstein | 6,216,104 | B1 | 4/2001 | Moshfeghi et al. |
| 5,933,809 | A | 8/1999 | Hunt et al. | 6,219,091 | B1 | 4/2001 | Yamanaka et al. |
| 5,935,085 | A | 8/1999 | Welsh et al. | 6,221,070 | B1 | 4/2001 | Tu et al. |
| 5,936,778 | A | 8/1999 | Miyano et al. | 6,234,958 | B1 | 5/2001 | Snoke |
| 5,941,817 | A | 8/1999 | Crawford | 6,238,799 | B1 | 5/2001 | Opolski |
| 5,950,168 | A | 9/1999 | Simborg et al. | 6,241,668 | B1 | 6/2001 | Herzog |
| 5,951,462 | A | 9/1999 | Yamanaka | 6,260,994 | B1 | 7/2001 | Matsumoto et al. |
| 5,956,416 | A | 9/1999 | Tsuruoka et al. | 6,272,470 | B1 | 8/2001 | Teshima |
| 5,956,689 | A | 9/1999 | Everhart | 6,275,255 | B1 | 8/2001 | Adair et al. |
| 5,956,690 | A | 9/1999 | Haggerson et al. | 6,283,960 | B1 | 9/2001 | Ashley |
| 5,959,613 | A | 9/1999 | Rosenberg et al. | 6,295,082 | B1 | 9/2001 | Dowdy et al. |
| 5,976,070 | A | 11/1999 | Ono et al. | 6,299,625 | B1 | 10/2001 | Bacher |
| 5,976,074 | A | 11/1999 | Moriyama | 6,309,347 | B1 | 10/2001 | Takahashi et al. |
| 5,980,454 | A | 11/1999 | Broome | 6,310,642 | B1 | 10/2001 | Adair et al. |
| 5,980,468 | A | 11/1999 | Zimmon | 6,319,196 | B1 | 11/2001 | Minami |
| 5,986,693 | A | 11/1999 | Adair et al. | 6,319,197 | B1 | 11/2001 | Tsuji et al. |
| 5,991,729 | A | 11/1999 | Barry et al. | 6,334,844 | B1 | 1/2002 | Akiba |
| 5,991,730 | A | 11/1999 | Lubin et al. | 6,346,075 | B1 | 2/2002 | Arai et al. |
| 5,999,168 | A | 12/1999 | Rosenberg et al. | 6,366,799 | B1 | 4/2002 | Acker et al. |
| 6,002,425 | A | 12/1999 | Yamanaka et al. | 6,381,029 | B1 | 4/2002 | Tipirneni |
| 6,007,482 | A | 12/1999 | Madni et al. | 6,398,724 | B1 | 6/2002 | May et al. |
| 6,007,531 | A | 12/1999 | Snoke et al. | 6,413,207 | B1 | 7/2002 | Minami |
| 6,014,630 | A | 1/2000 | Jeacock et al. | 6,421,078 | B1 | 7/2002 | Akai et al. |
| 6,015,088 | A | 1/2000 | Parker et al. | 6,425,535 | B1 | 7/2002 | Akiba |
| 6,017,322 | A | 1/2000 | Snoke et al. | 6,425,858 | B1 | 7/2002 | Minami |
| 6,020,875 | A | 2/2000 | Moore et al. | 6,436,032 | B1 | 8/2002 | Eto et al. |
| 6,020,876 | A | 2/2000 | Rosenberg et al. | 6,441,845 | B1 | 8/2002 | Matsumoto |
| 6,026,363 | A | 2/2000 | Shepard | 6,447,444 | B1 | 9/2002 | Avni et al. |
| 6,030,360 | A | 2/2000 | Biggs | 6,449,006 | B1 | 9/2002 | Shipp |
| 6,032,120 | A | 2/2000 | Rock et al. | 6,453,190 | B1 | 9/2002 | Acker et al. |
| 6,039,728 | A | 3/2000 | Berlien et al. | 6,454,162 | B1 | 9/2002 | Teller |
| 6,043,839 | A | 3/2000 | Adair et al. | 6,459,447 | B1 | 10/2002 | Okada et al. |
| 6,050,718 | A | 4/2000 | Schena et al. | 6,468,204 | B2 | 10/2002 | Sendai et al. |
| 6,057,828 | A | 5/2000 | Rosenberg et al. | 6,475,141 | B2 | 11/2002 | Abe |
| 6,059,719 | A | 5/2000 | Yamamoto et al. | 6,478,730 | B1 | 11/2002 | Bala et al. |
| 6,061,004 | A | 5/2000 | Rosenberg et al. | 6,489,987 | B1 | 12/2002 | Higuchi et al. |
| 6,067,077 | A | 5/2000 | Martin et al. | 6,496,827 | B2 | 12/2002 | Kozam et al. |
| 6,071,248 | A | 6/2000 | Zimmon | 6,498,948 | B1 | 12/2002 | Ozawa et al. |
| 6,075,555 | A | 6/2000 | Street | 6,503,193 | B1 | 1/2003 | Iwasaki et al. |
| 6,078,308 | A | 6/2000 | Rosenberg et al. | 6,520,908 | B1 | 2/2003 | Ikeda et al. |
| 6,078,353 | A | 6/2000 | Yamanaka et al. | 6,524,234 | B2 | 2/2003 | Ouchi |
| 6,078,876 | A | 6/2000 | Rosenberg et al. | 6,530,882 | B1 | 3/2003 | Farkas et al. |
| 6,080,104 | A | 6/2000 | Ozawa et al. | 6,533,722 | B2 | 3/2003 | Nakashima |
| 6,081,809 | A | 6/2000 | Kumagai | 6,540,669 | B2 | 4/2003 | Abe et al. |
| 6,083,152 | A | 7/2000 | Strong | 6,544,194 | B1 | 4/2003 | Kortenbach et al. |
| 6,083,170 | A | 7/2000 | Ben-Haim | 6,545,703 | B1 | 4/2003 | Takahashi et al. |
| 6,095,971 | A | 8/2000 | Takahashi | 6,551,239 | B2 | 4/2003 | Renner et al. |
| 6,099,465 | A | 8/2000 | Inoue | 6,558,317 | B2 | 5/2003 | Takahashi et al. |
| 6,100,874 | A | 8/2000 | Schena et al. | 6,561,971 | B1 | 5/2003 | Akiba |
| 6,104,382 | A | 8/2000 | Martin et al. | 6,565,507 | B2 | 5/2003 | Kamata et al. |
| 6,120,435 | A | 9/2000 | Eino | 6,574,629 | B1 | 6/2003 | Cooke, Jr. et al. |
| 6,125,337 | A | 9/2000 | Rosenberg et al. | 6,589,162 | B2 | 7/2003 | Nakashima et al. |
| 6,128,006 | A | 10/2000 | Rosenberg et al. | 6,595,913 | B2 | 7/2003 | Takahashi |
| 6,132,369 | A | 10/2000 | Takahashi | 6,597,390 | B1 | 7/2003 | Higuchi |
| 6,134,056 | A | 10/2000 | Nakamura | 6,599,239 | B2 | 7/2003 | Hayakawa et al. |
| 6,134,506 | A | 10/2000 | Rosenberg et al. | 6,602,186 | B1 | 8/2003 | Sugimoto et al. |
| 6,135,946 | A | 10/2000 | Konen et al. | 6,605,035 | B2 | 8/2003 | Ando et al. |
| 6,139,508 | A | 10/2000 | Simpson et al. | 6,609,135 | B1 | 8/2003 | Omori et al. |
| 6,141,037 | A | 10/2000 | Upton et al. | 6,611,846 | B1 | 8/2003 | Stoodley |
| 6,142,956 | A | 11/2000 | Kortenbach et al. | 6,612,624 | B1 * | 9/2003 | Segal et al. ............... 285/330 |
| 6,146,355 | A | 11/2000 | Biggs | 6,614,969 | B2 | 9/2003 | Eichelberger et al. |
| 6,149,607 | A | 11/2000 | Simpson et al. | 6,616,601 | B2 | 9/2003 | Hayakawa |
| 6,152,877 | A | 11/2000 | Masters | 6,623,424 | B2 | 9/2003 | Hayakawa et al. |

| Patent No. | Date | Inventor |
|---|---|---|
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Ohmori et al. |
| 6,682,479 B1 | 1/2004 | Takahashi et al. |
| 6,685,631 B2 | 2/2004 | Minami |
| 6,686,949 B2 | 2/2004 | Kobayashi et al. |
| 6,689,050 B1 * | 2/2004 | Beutter et al. ............... 600/117 |
| 6,690,409 B1 | 2/2004 | Takahashi |
| 6,690,963 B2 | 2/2004 | Ben-Haim et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B2 | 3/2004 | Benaron et al. |
| 6,715,068 B1 | 3/2004 | Abe |
| 6,716,162 B2 | 4/2004 | Hakamata |
| 6,728,599 B2 | 4/2004 | Wang et al. |
| 6,730,018 B2 | 5/2004 | Takase |
| 6,736,773 B2 | 5/2004 | Wendlandt et al. |
| 6,743,240 B2 | 6/2004 | Smith et al. |
| 6,749,559 B1 | 6/2004 | Krass et al. |
| 6,749,560 B1 | 6/2004 | Konstorum et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,414 B1 | 8/2004 | McStravick et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,553 B1 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B2 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,821 B2 | 9/2005 | Abe et al. |
| 6,943,822 B2 | 9/2005 | Iida et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,248 B2 | 9/2005 | Rudischhauser et al. |
| 6,950,691 B2 | 9/2005 | Uchikubo |
| 6,954,311 B2 | 10/2005 | Amanai |
| 6,955,671 B2 | 10/2005 | Uchikubo |
| 6,956,703 B2 | 10/2005 | Saito |
| 6,961,187 B2 | 11/2005 | Amanai |
| 6,962,564 B2 | 11/2005 | Hickle |
| 6,963,175 B2 | 11/2005 | Archenhold et al. |
| 6,964,662 B2 | 11/2005 | Kidooka et al. |
| 6,967,673 B2 | 11/2005 | Ozawa et al. |
| 6,974,466 B2 | 12/2005 | Ahmed et al. |
| 6,975,968 B2 | 12/2005 | Nakamitsu et al. |
| 6,976,954 B2 | 12/2005 | Takahashi |
| 6,977,053 B2 | 12/2005 | Mukasa et al. |
| 6,977,670 B2 | 12/2005 | Takahashi et al. |
| 6,980,227 B2 | 12/2005 | Iida et al. |
| 6,980,921 B2 | 12/2005 | Anderson et al. |
| 6,981,945 B1 | 1/2006 | Sarvazyan et al. |
| 6,982,740 B2 | 1/2006 | Adair et al. |
| 6,984,206 B2 | 1/2006 | Kumei et al. |
| 6,985,183 B2 | 1/2006 | Jan et al. |
| 6,986,686 B2 | 1/2006 | Shibata et al. |
| 6,994,668 B2 | 2/2006 | Miyano |
| 6,994,704 B2 | 2/2006 | Qin et al. |
| 7,001,330 B2 | 2/2006 | Kobayashi |
| 7,008,376 B2 | 3/2006 | Ikeda et al. |
| 7,204,821 B1 | 4/2007 | Clare |
| 7,238,010 B2 * | 7/2007 | Hershberger et al. ...... 417/477.2 |
| 7,413,542 B2 | 8/2008 | Kucklick |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193662 A1 | 12/2002 | Belson |
| 2002/0193664 A1 | 12/2002 | Ross et al. |

| | | |
|---|---|---|
| 2003/0032863 A1 | 2/2003 | Kazakevich |
| 2003/0065250 A1 | 4/2003 | Chiel et al. |
| 2003/0069897 A1 | 4/2003 | Roy et al. |
| 2003/0133011 A1 | 7/2003 | Amling |
| 2003/0149338 A1 | 8/2003 | Francois et al. |
| 2003/0181905 A1 | 9/2003 | Long |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0143159 A1 | 7/2004 | Wendlandt |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0075538 A1* | 4/2005 | Banik et al. ................. 600/141 |
| 2005/0192476 A1 | 9/2005 | Homan et al. |
| 2005/0197861 A1 | 9/2005 | Omori et al. |
| 2005/0200698 A1 | 9/2005 | Amling et al. |
| 2005/0203341 A1 | 9/2005 | Welker et al. |
| 2005/0203418 A1 | 9/2005 | Yamada et al. |
| 2005/0205958 A1 | 9/2005 | Taniguchi et al. |
| 2005/0207645 A1 | 9/2005 | Nishimura et al. |
| 2005/0209509 A1 | 9/2005 | Belson |
| 2005/0225872 A1 | 10/2005 | Uzawa et al. |
| 2005/0226508 A1 | 10/2005 | Gotohda |
| 2005/0228221 A1 | 10/2005 | Hirakawa |
| 2005/0228222 A1 | 10/2005 | Furumi |
| 2005/0228227 A1 | 10/2005 | Weber |
| 2005/0228697 A1 | 10/2005 | Funahashi |
| 2005/0231591 A1 | 10/2005 | Abe |
| 2005/0234507 A1 | 10/2005 | Geske et al. |
| 2005/0243169 A1 | 11/2005 | Ono et al. |
| 2005/0245898 A1* | 11/2005 | Wright et al. ................. 604/533 |
| 2005/0247081 A1 | 11/2005 | Sakata et al. |
| 2005/0250983 A1 | 11/2005 | Tremaglio et al. |
| 2005/0251112 A1 | 11/2005 | Danitz et al. |
| 2005/0251998 A1 | 11/2005 | Bar-Or et al. |
| 2005/0253044 A1 | 11/2005 | Kuriyama |
| 2005/0256370 A1 | 11/2005 | Fujita |
| 2005/0256373 A1 | 11/2005 | Bar-Or et al. |
| 2005/0256377 A1 | 11/2005 | Deppmeier et al. |
| 2005/0256424 A1 | 11/2005 | Zimmon |
| 2005/0264687 A1 | 12/2005 | Murayama |
| 2005/0267417 A1 | 12/2005 | Secrest et al. |
| 2005/0271340 A1 | 12/2005 | Weisburg et al. |
| 2005/0272978 A1 | 12/2005 | Brunnen et al. |
| 2005/0273085 A1 | 12/2005 | Hinmane et al. |
| 2005/0288545 A1 | 12/2005 | Matsumoto et al. |
| 2005/0288553 A1 | 12/2005 | Sugimoto |
| 2006/0015008 A1 | 1/2006 | Kennedy |
| 2006/0047185 A1 | 3/2006 | Shener |
| 2006/0047186 A1 | 3/2006 | Annecke |
| 2006/0068360 A1 | 3/2006 | Boulais |

FOREIGN PATENT DOCUMENTS

| | | |
|---|---|---|
| EP | 0 437 229 A1 | 7/1991 |
| EP | 0 689 851 A1 | 1/1996 |
| EP | 0 728 487 B1 | 8/1996 |
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 | 4/1994 |
| JP | 3372273 B2 | 4/1994 |
| JP | 06-254048 A | 9/1994 |
| JP | 3219521 B2 | 9/1994 |
| JP | 07-8441 A | 1/1995 |
| JP | 3482238 B2 | 12/1995 |
| JP | 10-113330 A | 5/1998 |
| JP | 10-286221 A | 10/1998 |
| JP | 11-216113 A | 8/1999 |
| JP | 2001 128933 A | 5/2001 |
| JP | 2002 078675 A | 3/2002 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 2003-75113 A | 3/2003 |
| JP | 2002 007134 A | 7/2003 |
| WO | WO 93/13704 A1 | 7/1993 |
| WO | WO 2004/016310 A2 | 2/2004 |
| WO | WO 2005/023082 A2 | 3/2005 |
| WO | 2006039512 A1 | 4/2006 |

* cited by examiner

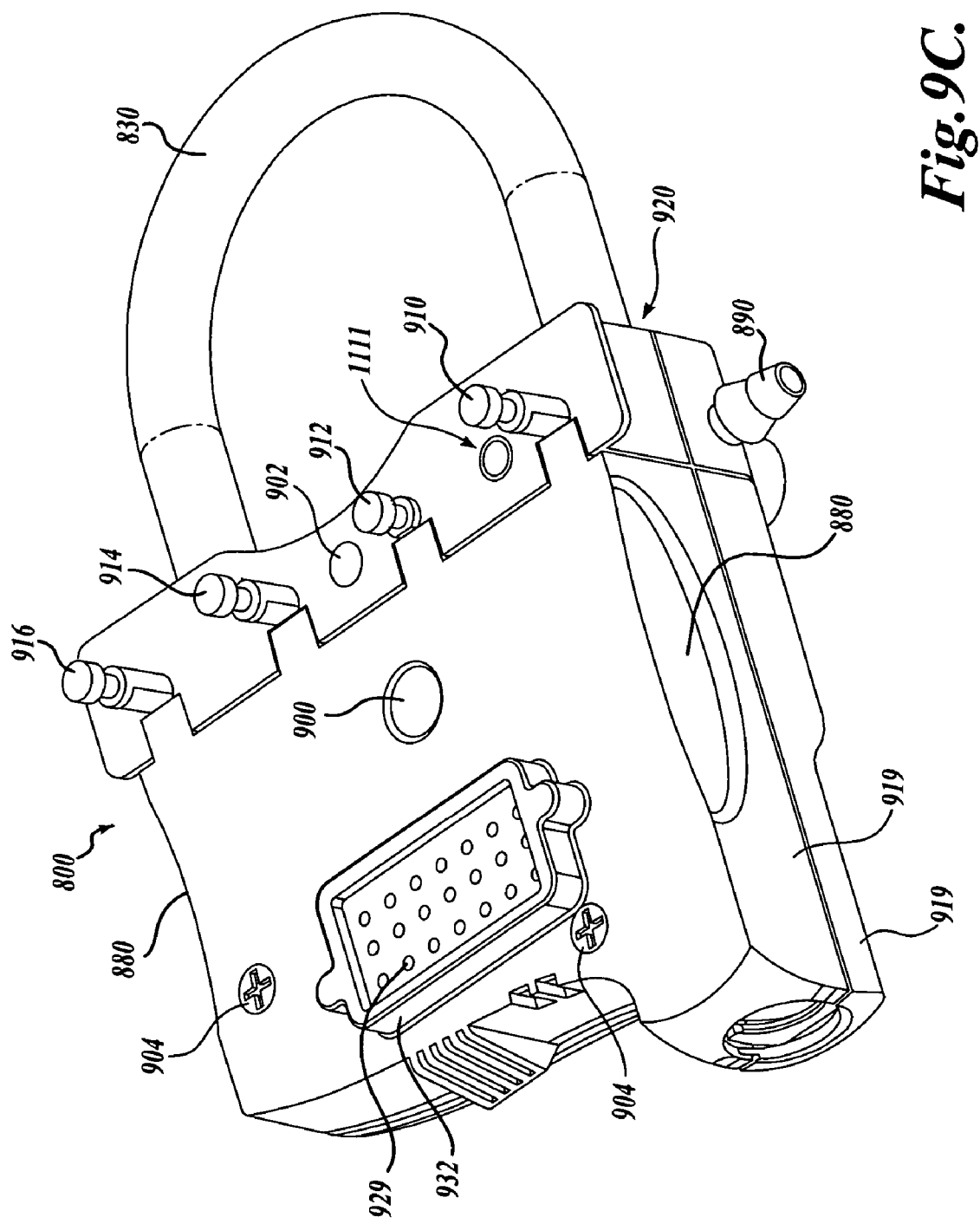

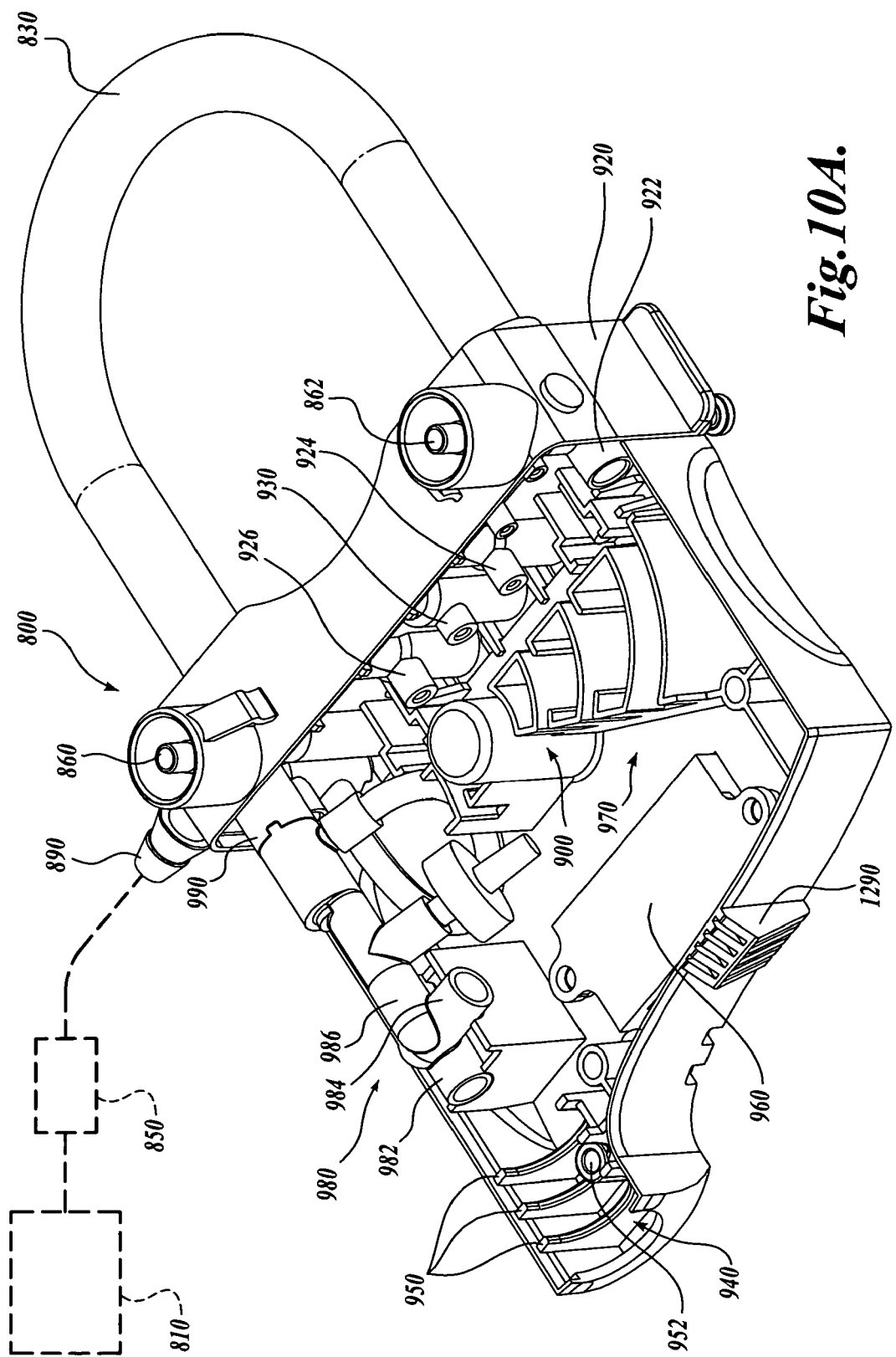

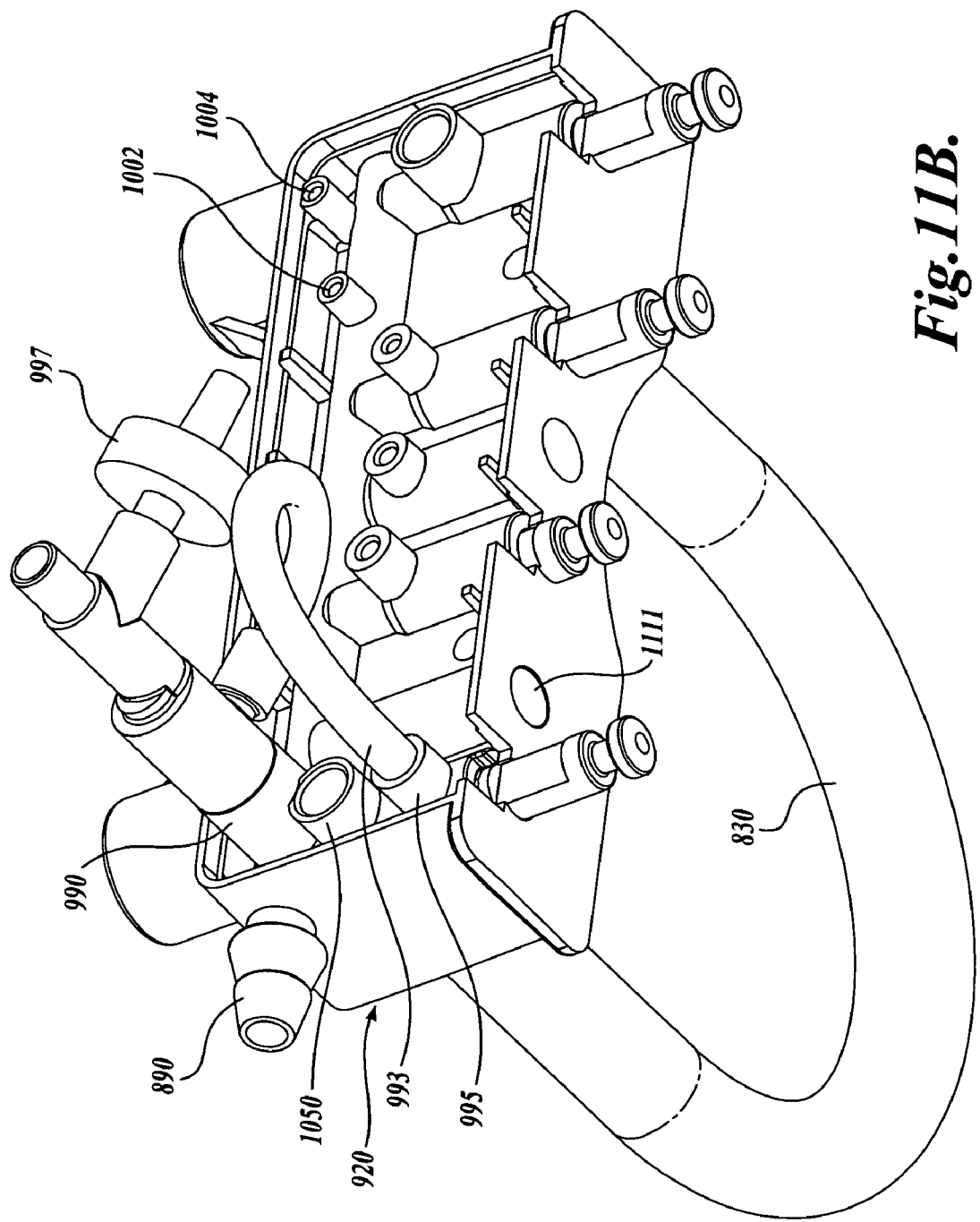

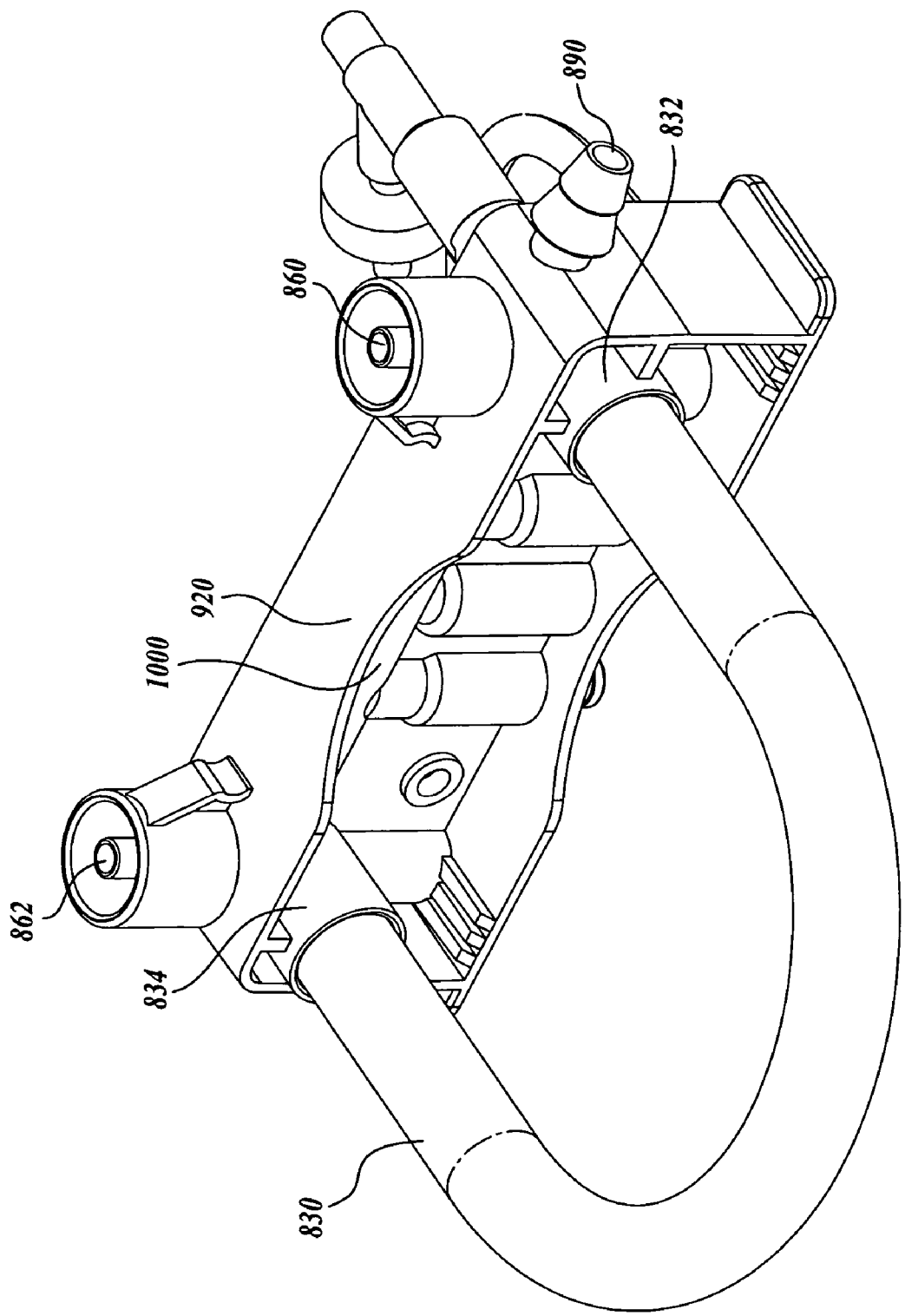

MULTI-FLUID DELIVERY SYSTEM

CROSS-REFERENCE TO RELATED APPLICATIONS

This application is a continuation-in-part of application Ser. No. 11/239,644, filed Sep. 29, 2005, which claims the benefit of U.S. Provisional Application No. 60/614,868, filed Sep. 30, 2004, both of which are incorporated herein by reference.

BACKGROUND

As an aid to the early detection of disease, it has become well established that there are major public health benefits that result from regular endoscopic examination of internal structures, such as the alimentary canals and airways, e.g., the esophagus, stomach, lungs, colon, uterus, ureter, kidney, and other organ systems. A conventional imaging endoscope used for such procedures is formed of a flexible shaft that has a fiber optic light guide that directs illuminating light from an external light source to the distal tip, where it exits the endoscope and illuminates the tissue to be examined. Frequently, additional optical components are incorporated, in order to adjust the spread of light exiting the fiber bundle at the distal tip. An objective lens and fiber optic imaging light guide communicating with a camera at the proximal end of the endoscope or an imaging camera chip installed at the distal tip produces an image that is displayed to the examiner. In addition, most endoscopes include one or more working channels, through which medical devices, such as biopsy forceps, snares, fulguration probes, and other tools, may be passed.

Navigating the endoscope shaft through complex and tortuous paths in a way that produces minimum pain, side effects, risk, or sedation to the patient is critical to the success of the examination. To this end, modem endoscopes include means for deflecting the distal tip of the endoscope to follow the pathway of the structure under examination, with minimum deflection or friction force upon the surrounding tissue. By manipulating a set of control knobs, the examiner is able to steer the endoscope during insertion and direct it to a region of interest, in spite of the limitations of such traditional control systems, which may be clumsy, non-intuitive, and friction-limited.

In any endoscopic procedure, there is almost always a need for the introduction and evacuation of different types of fluids, such as water, saline, drugs, contrast material, dyes, or emulsifiers. For example, one endoscopic procedure is a colonoscopy, which is an internal examination of the colon by means of an instrument called a colonoscope. In colonoscopy procedures, typically 5-10% of patients who arrive for the procedure are inadequately prepared (i.e., the colon is not properly cleared and flushed) and are, therefore, turned away. Some patients who are only marginally unprepared can be fully prepared by a physician or their assistant administering doses of liquid and aspirating the colon. However, these procedures are made more difficult and time consuming because it requires the physician to flush and evacuate stool or other debris, which represents a loss of productivity.

Another endoscopic procedure is an esophagogastroduodenoscopy (EGD), which is an examination of the lining of the esophagus, stomach, and upper duodenum by means of an endoscope that is inserted down the throat. During an EGD procedure, the mixing of bile and water creates a lot of captivating bubbles. These bubbles hinder the physician's visibility during the procedure. As a result, a liquid is often introduced to help reduce the bubbles and, thus, improve visibility.

Yet another endoscopic procedure is an endoscopic retrograde cholangiopancreatography (ERCP), which is an endoscopic procedure used to identify stones, tumors, or narrowing in the bile ducts. In an ERCP procedure, fluids are used to flush away bleeding from sites. In addition, it is sometimes helpful to introduce dyes for providing contrast to the site. Contrast material, or contrast dye, is a substance used to make specific organs, blood vessels, or types of tissue (such as tumors) more visible on X-rays. Common contrast material substances include iodine, barium, and gadolinium.

Conventional endoscopes allow the introduction of liquids via a separate delivery device, such as a syringe or injection catheter that is passed through its working channel, in order to deliver the liquid to the distal tip of the endoscope to the target site within a patient's body. This liquid delivery method involves several steps that include, for example, the user selecting a large capacity syringe (e.g., up to 100 cc), the user pouring a desired liquid into a bowl, the user drawing the liquid into the syringe, the user attaching the syringe to the working channel of the endoscope, and the user squeezing the liquid out of the syringe. This cumbersome and time-consuming process is repeated for any and all types of liquids required in any given endoscopic procedure.

To overcome these and other problems, there is a need for an endoscope having a simplified way to introduce one or more liquids, such as water, saline, drugs, contrast material, dyes, or emulsifiers, that are used in endoscopic procedures, such as a colonoscopy procedure, an EGD procedure, or an ERCP procedure, etc. The endoscopic system should have improved simplicity and ease of use, increased efficiency, and greater clinical productivity and patient throughput. Furthermore, there is a need for improved control of the delivery rate of a liquid and improved mechanisms for mixing two or more fluids. Finally, there is a need for an endoscope that can deliver one or more liquids during a procedure and be inexpensive enough to manufacture that the device can be disposable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a fluid delivery system for use with an endoscope. The fluid delivery system includes an imaging endoscope that may be used in combination with multiple fluid delivery mechanisms. In one embodiment, the imaging endoscope may be designed such that it is sufficiently inexpensive to manufacture that it may be considered a single-use, disposable item.

Certain embodiments of the invention include a single, large fluid source and pump installed upon a reusable operator console in combination with a small, fluid reservoir and pump installed within a proximal connector of the imaging endoscope. Other embodiments of the invention include multiple fluid sources that feed a common fluid channel and that are pressurized by a common pump. Yet other embodiments of the invention include multiple fluid sources that feed dedicated fluid channels that are pressurized by dedicated pumps, respectively. Yet other embodiments of the invention include a small, fluid reservoir and pump installed within a handheld manual controller of the imaging endoscope or on the proximal connector itself. The multi-fluid endoscopic systems of the present invention provide the user with the flexibility of changing fluids either in advance of a procedure or on-the-fly as needed, instead of relying on fixed fluid sources only. Furthermore, the arrangement of fluid sources, pumps and valves within the multi-fluid endoscopic systems of the present invention provide a controlled fluid delivery rate and a controlled way of mixing fluids.

In yet another embodiment of the invention, the endoscope includes a proximal connector, including a manifold that delivers a fluid to one or more lumens in the endoscope. Valve pistons or spools are selectively actuated to deliver a pressurized liquid to one or more of its lumens. The proximal connector can be attached to and detached from an interface assembly between the console and the proximal endoscopic shaft leading to the control handle.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 9C illustrates a rear surface of a proximal connector in accordance with an embodiment of the present invention;

FIG. 10A is a cutaway view of the proximal connector in accordance with an embodiment of the present invention;

FIGS. 11A, 11B, and 11C illustrate a manifold within the proximal connector in accordance with an embodiment of the present invention;

DETAILED DESCRIPTION

Figure 1:
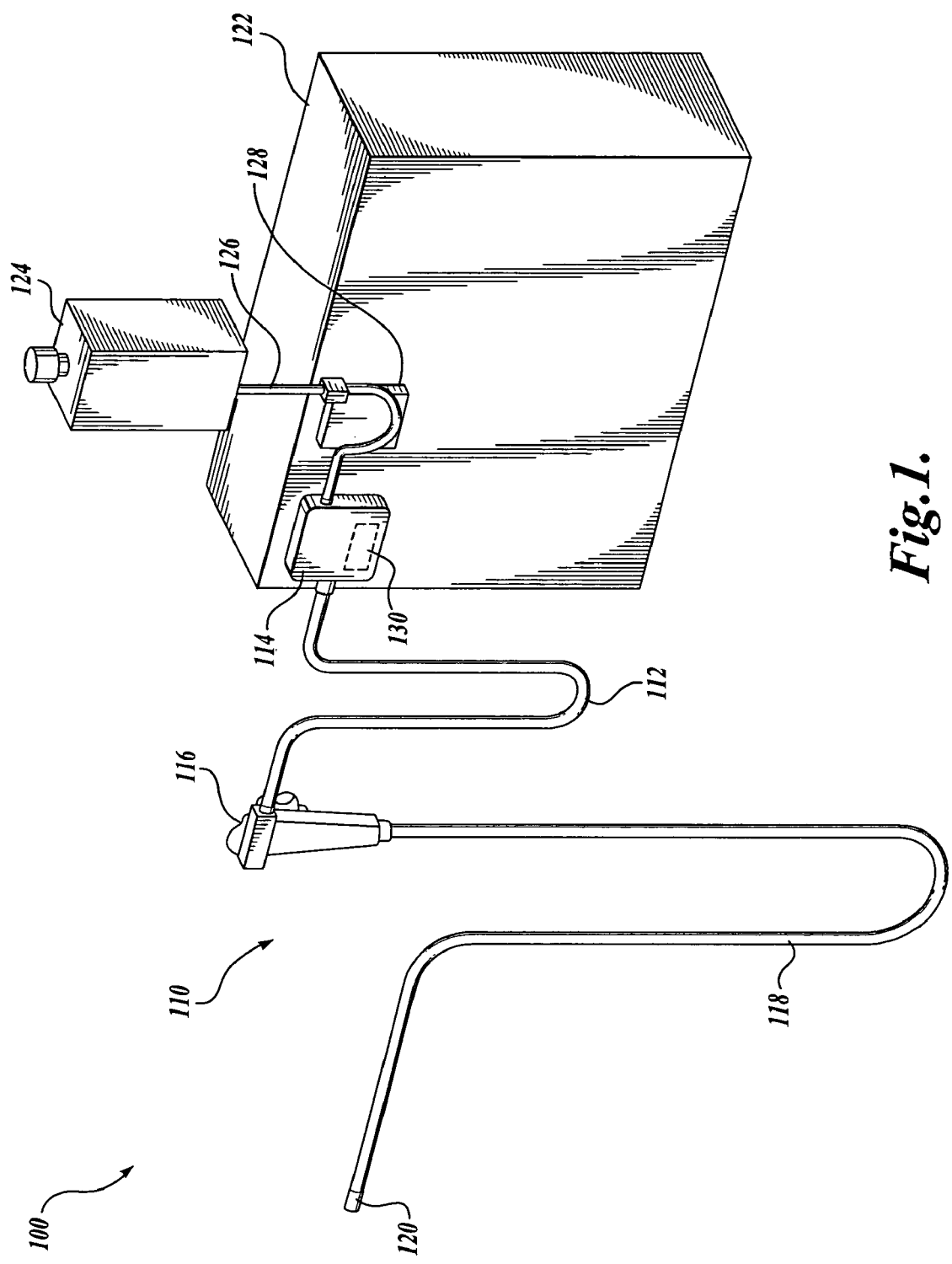
FIG. 1 illustrates a perspective view of a multi-fluid endoscopic system in accordance with an embodiment of the invention.

FIG. 1 illustrates a perspective view of an endoscopic system 100 in accordance with a first embodiment of the invention. The endoscopic system 100 includes an imaging endoscope 110 that further includes an endoscope proximal shaft 112 that is electrically, mechanically, and fluidly connected, at one end, to an endoscope proximal connector 114 and, at an opposite end, to an inlet port of a handheld manual controller 116, and an endoscope distal shaft 118 that is electrically, mechanically, and fluidly connected, at one end, to an output port of handheld manual controller 116. The endoscope distal tip 120 is located at the opposite end for advancing into a patient's body.

Imaging endoscope 110 is an instrument that allows for the examination of the interior of a tract, lumen or vessel or hollow organ of a patient. Imaging endoscope 110 further includes an illumination mechanism, an image sensor, and an elongated shaft that has one or more lumens located therein. Imaging endoscope 110 may be sufficiently inexpensive to manufacture, such that it is considered a single-use, disposable item, such as is described in reference to U.S. patent application Ser. No. 10/406,149 filed Apr. 1, 2003, Ser. No. 10/811,781, filed Mar. 29, 2004, and Ser. No. 10/956,007, filed Sep. 30, 2004, and International Application No. PCT/US2005/035479, filed Sep. 30, 2005, published Apr. 13, 2006, under No. WO 2006/039646A2, all assigned to Scimed Life Systems, Inc./Boston Scientific Scimed, Inc., which are incorporated herein by reference. The referenced patent applications describe an endoscope imaging system that includes a reusable control cabinet that has a number of actuators or a manually operated handle on the endoscope that controls the orientation of an endoscope that is connectable thereto. The endoscope is used with a single patient and is then disposed. This assures a sterile instrument for each use. The endoscope includes an illumination mechanism, an image sensor, and an elongated shaft that has one or more lumens located therein. An articulation joint at the distal end of the endoscope allows the distal end to be oriented by the actuators in the control cabinet or by manual control.

The endoscopic system 100 further includes an operator console 122 that is electrically connected to standard I/O devices, such as a video display and a keyboard. A fluid source 124 is fluidly connected to the endoscope proximal connector 114 of imaging endoscope 110 via a length of tubing 126 that passes through a pump 128 or in another way to achieve the desired flow, such as gravity feed. Fluid source 124 serves as a reservoir that contains a supply of liquid, such as water or saline, for use during a medical procedure. Fluid source 124 may take the form of a rigid vessel or a bladder with a capacity of, for example, up to one liter of fluid. Fluid source 124 may be a refillable vessel, or alternatively, fluid source 124 is sufficiently inexpensive to manufacture that it is considered a single-use, disposable item. Tubing 126 is a length of any standard flexible tubing, for example, ¼-inch tubing, which is also sufficiently inexpensive to manufacture, such that it is considered a single-use, disposable item. Pump 128 is, for example, a standard peristaltic pump that is used to withdraw liquid from fluid source 124 on demand. A peristaltic pump works by means of rollers on rotating arms that pinch the flexible tubing against an arc and, thus, move the fluid along. Pump 128 is capable of delivering, for example, up to 65 pounds/square inch (PSI) of pressure for a flow rate of, for example, 600 ml/min.

In one embodiment, the endoscope proximal connector 114 of imaging endoscope 110 is electrically and mechanically connected to the exterior of operator console 122, as shown in FIG. 1, via a quick-release mechanism for making and breaking all electrical, mechanical, and fluid/air/vacuum connections. The quick-release mechanism allows endoscope proximal connector 114 to be secured easily to the exterior of operator console 122. Endoscope proximal connector 114 includes wires and tubes that pass through endoscope proximal shaft 112, then through a handheld manual controller 116, then through endoscope distal shaft 118, and then to endoscope distal tip 120. Additionally, mounted within endoscope proximal connector 114 can be another fluid reservoir that has an associated pump mounted within operator console 122 or controller 116. Endoscope proximal connector 114 and the additional fluid reservoir are described in more detail below with reference to FIG. 2.

Endoscope proximal shaft 112 and endoscope distal shaft 118 are formed of a suitably lightweight, flexible material, such as polyurethane or other biocompatible materials. Endoscope proximal shaft 112 and endoscope distal shaft 118 are elongated shafts that have one or more lumens located therein and wiring located therein to support, for example, a working channel, a jet wash mechanism, an illumination mechanism, and an image sensor located at endoscope distal tip 120. Also included within handheld manual controller 116 and endoscope distal shaft 118 are the electrical and mechanical mechanisms for articulating endoscope distal tip 120 for manually advancing into a patient.

Handheld manual controller 116 of imaging endoscope 110 is a handheld device that is electrically and mechanically connected to operator console 122. Handheld manual controller 116 accepts inputs from a human operator via standard push buttons, rotary knobs, joysticks, or other activation devices, either singularly or in combination, to control the operation of imaging endoscope 110, which includes the delivery of pressurized liquid from fluid source 124. Alternatively, a user input device such as a keyboard or other user interface located remotely from the endoscope may accept inputs from a human operator to control the operation of the imaging endoscope 110, including the delivery of pressurized liquid from fluid source 124.

Operator console 122 is a special-purpose electronic and electromechanical apparatus that facilitates, processes, and manages all functions of multi-fluid endoscopic system 100. Operator console 122 is loaded with software for managing, for example, the operation of imaging endoscope 110 and its associated imaging electronics in order to create and/or transfer images received from an image sensor within imaging endoscope 110 to the video display for viewing by a user, and/or video capture. Operator console 122 further manages the operation of all pumps, such as pump 128.

Figure 2:
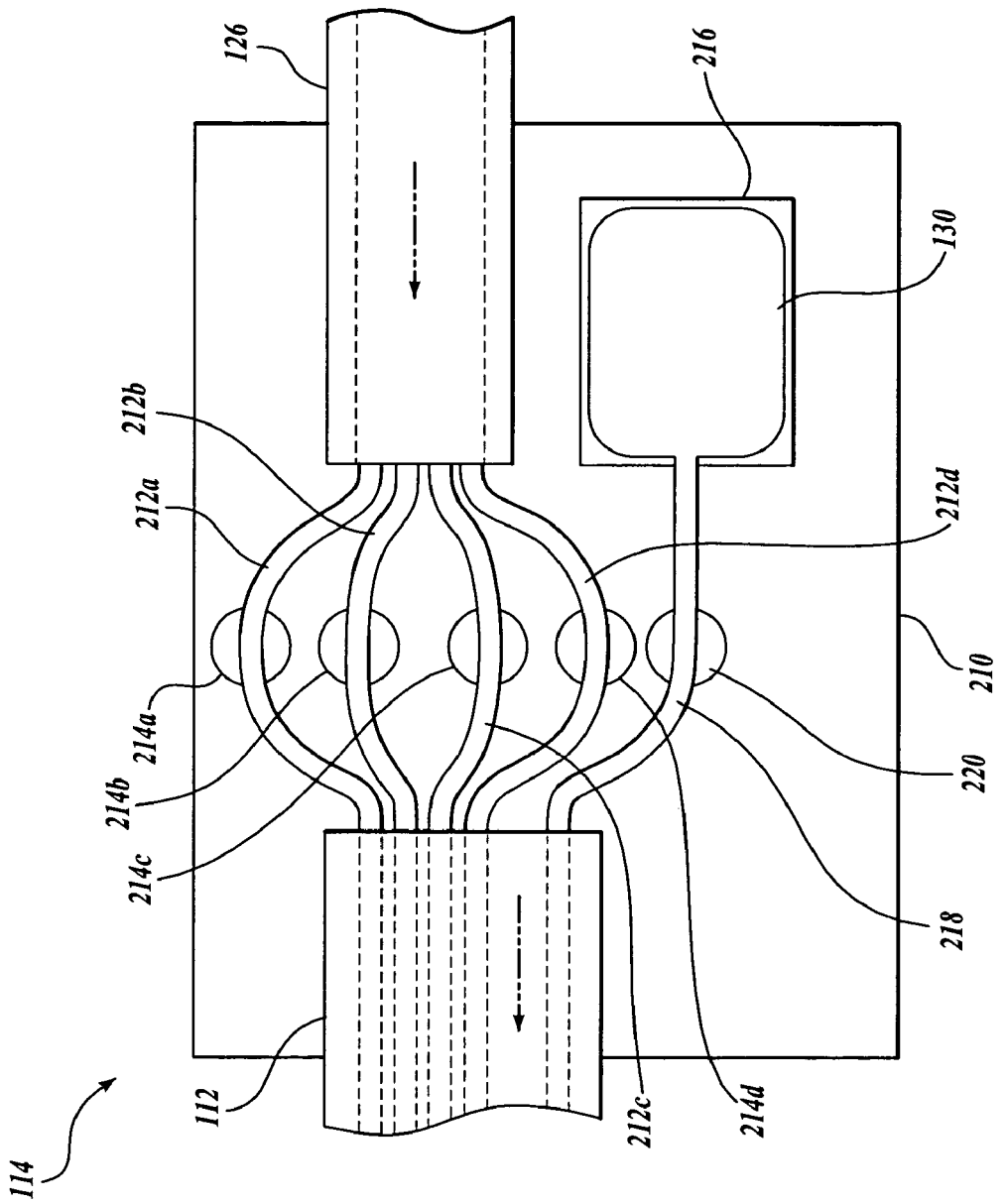
FIG. 2 illustrates a side view of an endoscope proximal connector in accordance with an embodiment of the invention.

FIG. 2 illustrates a side view of an exemplary endoscope proximal connector 114 in accordance with an embodiment of the present invention. Endoscope proximal connector 114 includes a proximal connector housing 210 that is formed of a suitably lightweight, rigid material, such as molded plastic. An end of tubing 126, which is a single fluid channel, is split into an arrangement of multiple fluid channels 212, for example, fluid channels 212a, 212b, 212c, and 212d. Fluid channels 212a, 212b, 212c, and 212d are fed separately into and along the full length of endoscope proximal shaft 112 to endoscope distal tip 120.

Fluid channels 212a, 212b, 212c, and 212d are used, for example, for supplying fluid, such as water, from fluid source 124 via pump 128 for (1) cooling light-emitting diodes (LEDs) (i.e., the illumination mechanism), (2) supplying a low pressure bolus wash, (3) supplying a high pressure jet wash, and (4) supplying a lens wash, all of which are located at endoscope distal tip 120. Multiple fluid channels 212 are controlled via multiple respective pinch valves 214. More specifically, fluid channels 212a, 212b, 212c, and 212d are controlled via pinch valves 214a, 214b, 214c, and 214d, respectively. Pinch valves 214 are standard valves, within which the flexible tubing of fluid channels 212 is pinched between one or more moving external elements, in order to regulate the flow of fluid.

FIG. 2 also shows a fluid reservoir 130 fitted into a recessed cavity 216 within endoscope proximal connector 114. Fluid reservoir 130 is fluidly connected to a fluid channel 218 that is fed into and along the full length of endoscope proximal shaft 112 and delivers the fluid from fluid reservoir 130 to endoscope distal tip 120. The flow of fluid is controlled by a pinch valve 220 that is identical to pinch valves 214. Fluid reservoir 130 is in the form of, for example, a disposable, soft, flexible bag or bladder that is easily detachable from fluid channel 218. The capacity of liquid held within fluid reservoir 130 is relatively small, compared with the capacity of fluid source 124. Fluid reservoir 130 may be sized, for example, to hold a small quantity of irrigation liquids, contrast media, medication, or dyes for marking tissue. An access door may be included within proximal connector housing 210 for installing or removing fluid reservoir 130 as needed before, after, or during a medical procedure. The liquid within fluid reservoir 130 may be pressurized with any well-known mechanisms, such as a piston that pushes against the bladder that forms fluid reservoir 130. Additionally, electrical wires pass through endoscope proximal connector 114 between handheld manual controller 116 and operator console 122 for controlling the flow of fluids via the combined functions of pinch valves 214a, 214b, 214c, or 214d and pump 128 and/or pinch valve 220 and the pressurizing mechanism of fluid reservoir 130.

In operation, and with continuing reference to FIGS. 1 and 2, pressurized fluids from fluid source 124 and/or fluid reservoir 130 are delivered along the full length of endoscope proximal and distal shafts 112, 118 to endoscope distal tip 120, on demand, under the control of electronics located within operator console 122. More specifically, pump 128 and the pressurizing mechanism of fluid reservoir 130 are activated, and the user controls the on-demand delivery of fluid, for example, to supply a low pressure bolus wash via the working channel of imaging endoscope 110, to supply a high pressure jet wash at endoscope distal tip 120, or to supply a lens wash at endoscope distal tip 120, all via push buttons on handheld manual controller 116 that control pinch valves 214a, 214b, 214c, or 214d. Additionally, the user controls the on-demand delivery of fluid from fluid reservoir 130 via a push button on handheld manual controller 116 that controls pinch valve 220 and the pressurizing mechanism of fluid reservoir 130, for example, to deliver medication or dye through endoscope distal shaft 118 of imaging endoscope 110 and out of endoscope distal tip 120 to a tissue site within the patient. Pressurized fluids from fluid source 124 and/or fluid reservoir 130 may be delivered continuously to the endoscope distal tip 120 to supply cooling to the LEDs.

Figure 3:
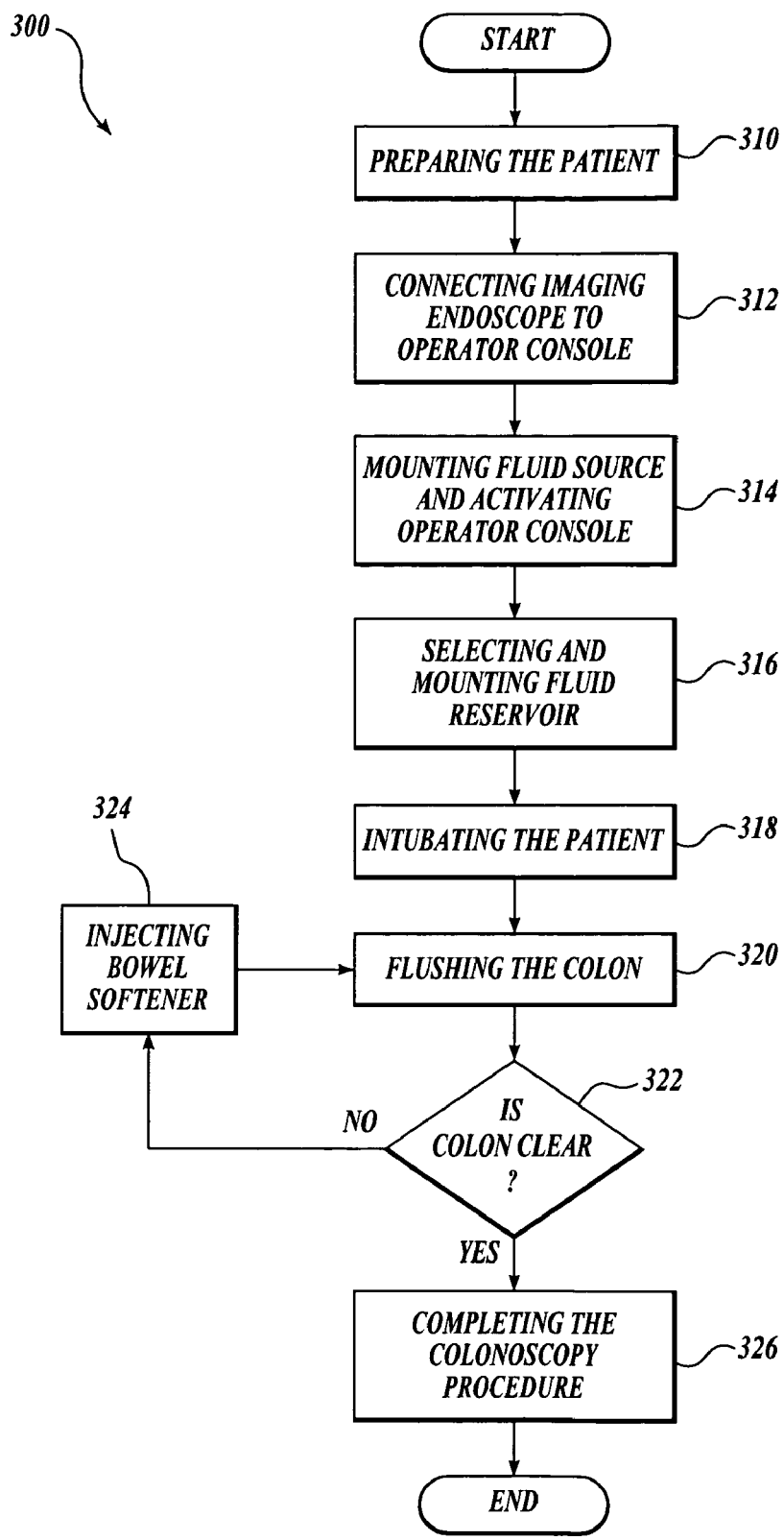
FIG. 3 illustrates a flow diagram of an exemplary method of using a multi-fluid endoscopic system of the present invention during a colonoscopy procedure.

FIG. 3 is a flow diagram of an exemplary method 300 of using multi-fluid endoscopic system 100 to handle a poorly prepared patient during a colonoscopy procedure in accordance with the invention. Method 300 and multi-fluid endoscopic system 100 are not limited to a colonoscopy procedure. Those skilled in the art will recognize that the method steps of method 300 may be adapted easily to apply to any of the various medical procedures that use various types of fluid sources, respectively. Method 300 includes the steps of:

Step 310: Preparing the Patient

In this step, in a predetermined time period prior to the time of the colonoscopy procedure, a patient consumes a quantity of, for example, a phosphosoda solution or a colyte solution, which serves as a laxative to flush stool out of the patient's colon. Alternatively, the patient arrives with no or insufficient preparation and the physician manually clears the patient's colon with a colon preparation endoscope. Method 300 proceeds to step 312.

Step 312: Connecting Imaging Endoscope to Operator Console

In this step, a user, which may be a physician, nurse, or other assistant, attaches endoscope proximal connector 114 of imaging endoscope 110 to the side of operator console 122 and thereby makes all electrical and fluid connections to operator console 122. The user activates operator console 122. Method 300 proceeds to step 314.

Step 314: Mounting Fluid Source and Activating Operator Console

In this step, a user mounts fluid source 124 to operator console 122 and, subsequently, connects tubing 126, at one end, to the outlet of fluid source 124 and, at the opposite end, to a port of endoscope proximal connector 114, while, at the same time, passing a portion of tubing 126 within pump 128. The user then activates operator console 122. Method 300 proceeds to step 316.

Step 316: Selecting and Mounting Fluid Reservoir

In this step, a user selects a fluid reservoir 130 that contains the type of liquid required for the medical procedure, such as a bowel softener in the case of a colonoscopy procedure and, subsequently, mounts fluid reservoir 130 within cavity 216 of endoscope proximal connector 114. Method 300 proceeds to step 318.

Step 318: Intubating the Patient

In this step, under the control of operator console 122 and by using the controls of handheld manual controller 116, the physician intubates the patient, by introducing and advancing endoscope distal tip 120 of imaging endoscope 110 into a body cavity of the patient, until such time that the area of the colon to be cleared may be visualized upon video display of operator console 22. Method 300 proceeds to step 320.

Step 320: Flushing the Colon

In this step, under the control of operator console 122 and by using the controls of handheld manual controller 116, the user alternately flushes and aspirates the patient's colon, by alternately activating the bolus wash and/or jet wash function and a suction function of multi-fluid endoscopic system 100. Aspiration can be through the working channel, back to a vacuum source (typically a house source) with an appropriate trap for solid matter. In doing so, the user controls the activation of pump 128, one or more pinch valves 214, and the connection to the suction/vacuum source via the controls of handheld manual controller 116. Method 300 proceeds to step 322.

Step 322: Is Colon Clear?

In this decision step, the user visualizes the colon by using the imaging electronics at endoscope distal tip 120, in combination with the video display of operator console 122, to determine whether the bolus wash and/or jet wash of step 320 is effective in breaking down the stool in the patient's colon and, thus, renders the colon clear. If yes, method 300 proceeds to step 326. If no, method 300 proceeds to step 324.

Step 324: Injecting Bowel Softener

In this step, under the control of operator console 122 and by using the controls of handheld manual controller 116, the user injects a bowel softener to help emulsify the stool by controlling pinch valve 220, such that the bowel softener within fluid reservoir 130 that is mounted within endoscope proximal connector 114 is released and, thus, passes into the patient's colon via fluid channel 218 of endoscope proximal shaft 112. Method 300 returns to step 320.

Step 326: Completing the Colonoscopy Procedure

In this step, under the control of operator console 122 and by using the controls of handheld manual controller 116, the user completes the colonoscopy procedure which may include such steps as selecting another type of liquid for installing into fluid reservoir 130 within cavity 216 of endoscope proximal connector 114. Such fluids include, for example, an India ink for marking a tissue site. Method 300 then ends.

Figure 4:
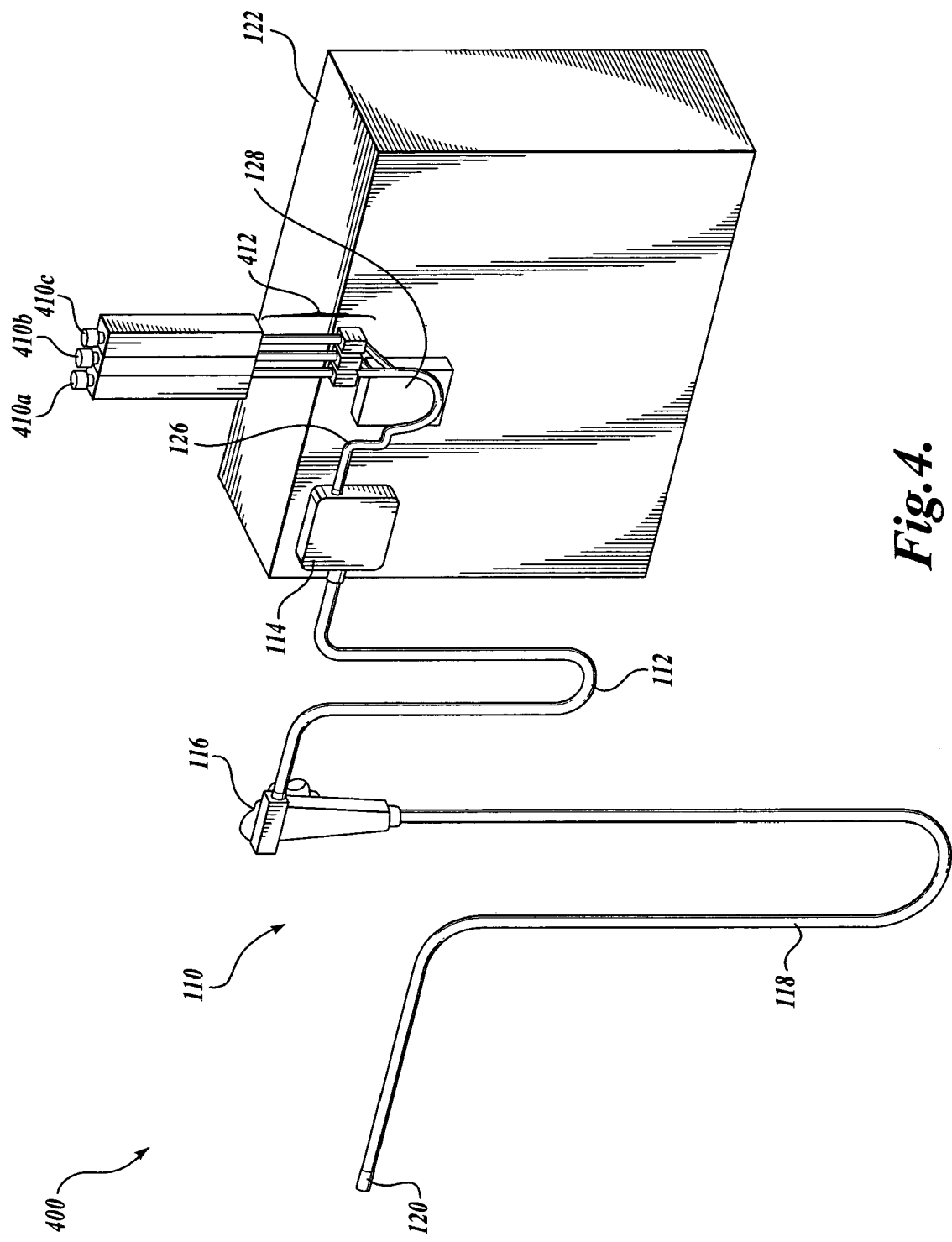
FIG. 4 illustrates a perspective view of a multi-fluid endoscopic system in accordance with another embodiment of the invention.

FIG. 4 illustrates a perspective view of a multi-fluid endoscopic system 400 in accordance with a second embodiment of the invention. Multi-fluid endoscopic system 400 includes imaging endoscope 110 that is connected to operator console 122 via endoscope proximal connector 114, as described in reference to FIGS. 1 and 2. Multi-fluid endoscopic system 400 includes pump 128, as described in reference to FIG. 1. Multi-fluid endoscopic system 400 further includes a plurality of fluid sources 410, e.g., a fluid source 410a, 410b, and 410c, that feed tubing 126 via a tubing subassembly 412 that brings together the tubing from the separate fluid sources 410 to a common line, i.e., tubing 126, and wherein each fluid source 410 has an associated pinch valve that allows liquid to reach the pump 128. Each fluid source 410 may take the form of a rigid vessel or a bladder with a capacity of, for example, up to one liter of fluid. Each fluid source 410 may be a refillable vessel, or alternatively, each fluid source 410 is sufficiently inexpensive to manufacture, such that it is considered a single-use, disposable item.

In operation and with reference to FIG. 4, pressurized fluids are delivered along the full length of endoscope proximal shaft 112 to endoscope distal tip 120 on demand, under the control of electronics located within operator console 122, in similar fashion as described in reference to the endoscopic system 100 of FIG. 1. However, the inclusion of multiple fluid sources 410 in the endoscopic system 100 allows multiple fluid types, such as saline, irrigation liquids, medication, or dyes, to be delivered, singly or mixed with one another, to imaging endoscope 110, under the control of operator console 122 and in combination with handheld manual controller 116 for controlling pump 128 and the pinch valves of tubing sub-assembly 412. Furthermore, endoscope proximal connector 114 may include multiple fluid channels 212 and fluid reservoir 130, as described in reference to FIG. 2 or, optionally, may include a greater or lesser number of fluid channels 212 and not include fluid reservoir 130 of the type illustrated in FIG. 2.

Figure 5:
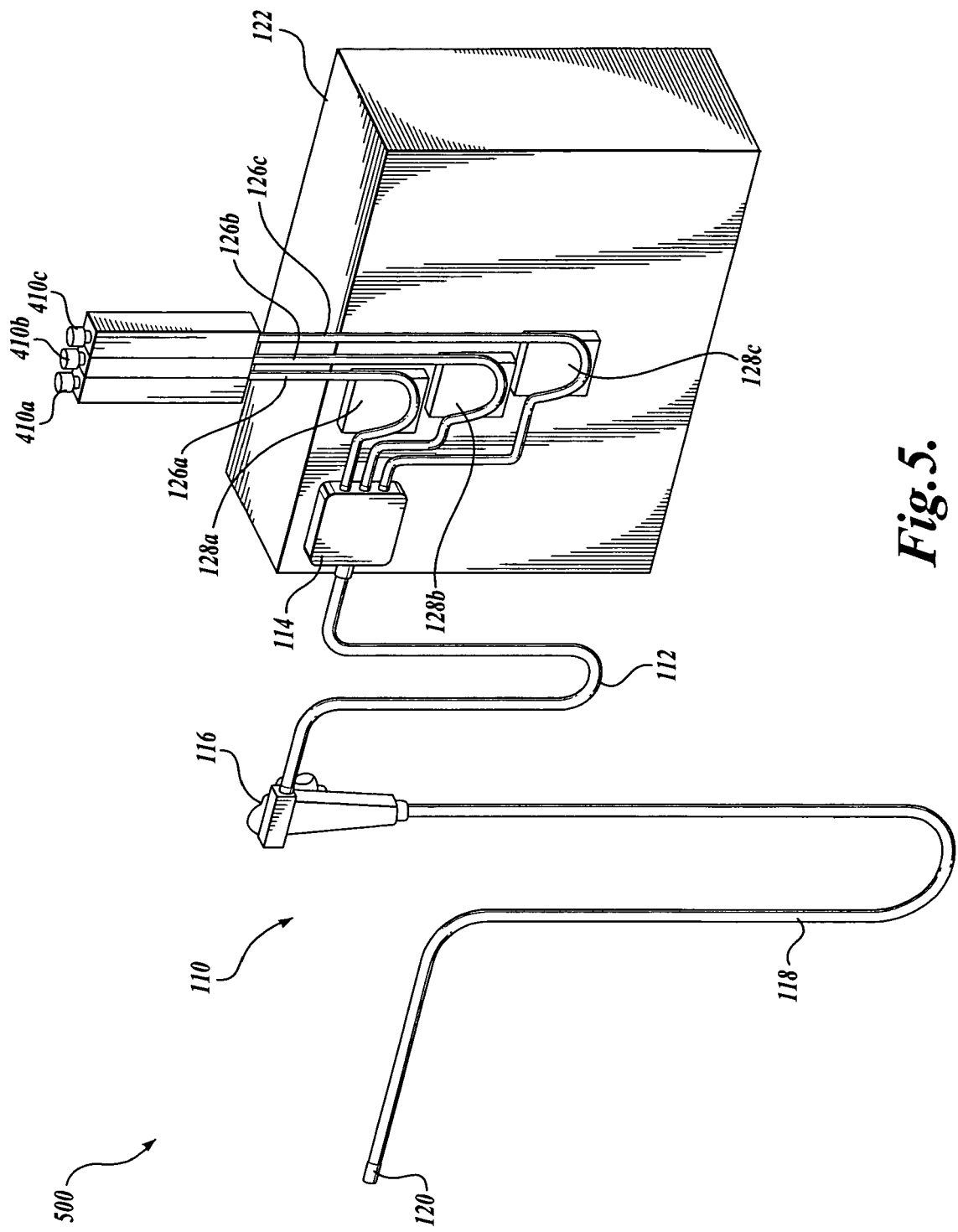
FIG. 5 illustrates a perspective view of a multi-fluid endoscopic system in accordance with another embodiment of the invention.

FIG. 5 illustrates a perspective view of a multi-fluid endoscopic system 500 in accordance with a third embodiment of the invention. Multi-fluid endoscopic system 500 includes imaging endoscope 110 that is connected to operator console 122 via endoscope proximal connector 114, as described in reference to FIGS. 1 and 2. Multi-fluid endoscopic system 400 also includes multiple fluid sources 410, e.g., fluid source 410a, 410b, and 410c, as described in reference to FIG. 4. However, instead of including tubing sub-assembly 412, each fluid source 410 has its own dedicated length of tubing 126 and dedicated pump 128 that feed endoscope proximal connector 114 of imaging endoscope 110. For example, fluid source 410a is fluidly connected to endoscope proximal connector 114 via a length of tubing 126a that passes through pump 128a, fluid source 410b is fluidly connected to endoscope proximal connector 114 via a length of tubing 126b that passes through pump 128b, and fluid source 410c is fluidly connected to endoscope proximal connector 114 via a length of tubing 126c that passes through pump 128b, as shown in FIG. 5. Each fluid source 410, therefore, has its own dedicated fluid channel 212 and pinch valve 214 within endoscope proximal connector 114. The dedicated fluid channels 212 pass along the full length of endoscope proximal shaft 112 to endoscope distal tip 120.

In operation and with reference to FIG. 5, pressurized fluids are delivered along the full length of endoscope proximal shaft 112 to endoscope distal tip 120 on demand, under the control of electronics located within operator console 122, in similar fashion as described in reference to multi-fluid endoscopic system 100 of FIG. 1. However, the inclusion of multiple fluid sources 410 in multi-fluid endoscopic system 100 allows multiple fluid types, such saline, irrigation liquids, medication, or dyes, to be delivered via a dedicated fluid channel 212 to imaging endoscope 110, under the control of operator console 122, in combination with handheld manual controller 116, for controlling pumps 128a, 128b, and 128c and associated pinch valves 214a, 214b, and 214c within endoscope proximal connector 114. Optionally, endoscope proximal connector 114 may not include fluid reservoir 130.

Figure 6:
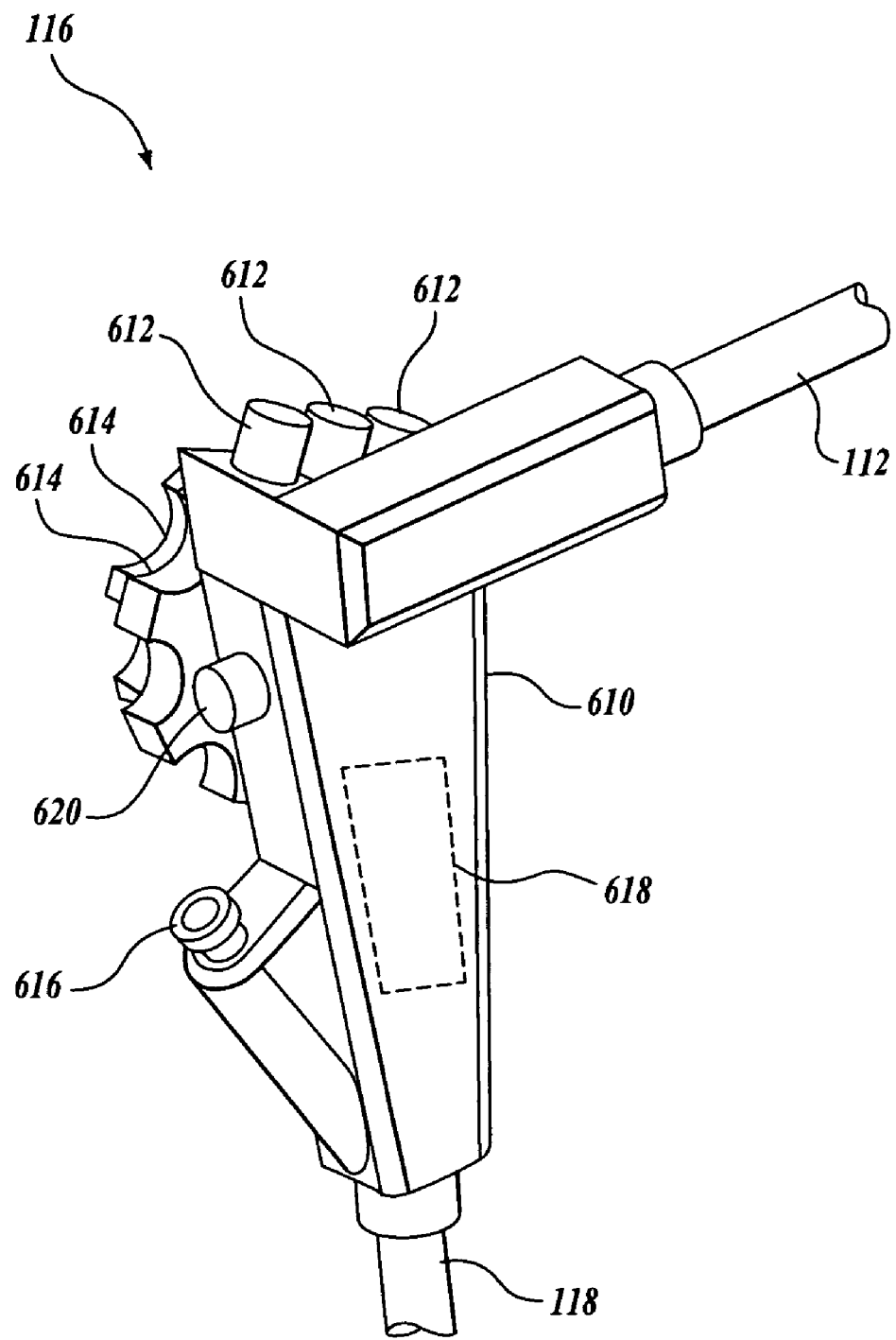
FIG. 6 illustrates a perspective view of a handheld manual controller that includes a local fluid reservoir in accordance with an embodiment of the invention.

FIG. 6 illustrates a perspective view of handheld manual controller 116 that includes a local fluid reservoir in accordance with another embodiment of the invention. FIG. 6 shows that handheld manual controller 116 includes a controller housing 610 formed of a suitably lightweight, rigid material, such as molded plastic. Controller housing 610 is electrically, mechanically, and fluidly connected, at one end, to endoscope proximal shaft 112 and, at an opposite end, to endoscope distal shaft 118. Mounted within controller housing 610 of handheld manual controller 116 are a plurality of control buttons 612 that allow the physician to manipulate the functions of the endoscope, such as taking a picture, activating light, activating water, activating air, or activating suction at endoscope distal tip 120. A plurality of rotary knobs 614 control the articulation of endoscope distal tip 120 for manually advancing into the patient, and a working channel access port 616 allows the insertion of a therapeutic or diagnostic instrument into the working channel of endoscope distal shaft 118.

In the example shown in FIG. 6, handheld manual controller 116 provides an alternative to having a fluid reservoir located within endoscope proximal connector 114, such as fluid reservoir 130, as described in reference to FIGS. 1 and 2. In this example, handheld manual controller 116 further includes an integrated fluid reservoir 618 that has an associated fluid activation button 620, which provides a conveniently located mechanism for activating the delivery of fluid from integrated fluid reservoir 618. Integrated fluid reservoir 618 is described in more detail in reference to FIG. 7.

Figure 7:
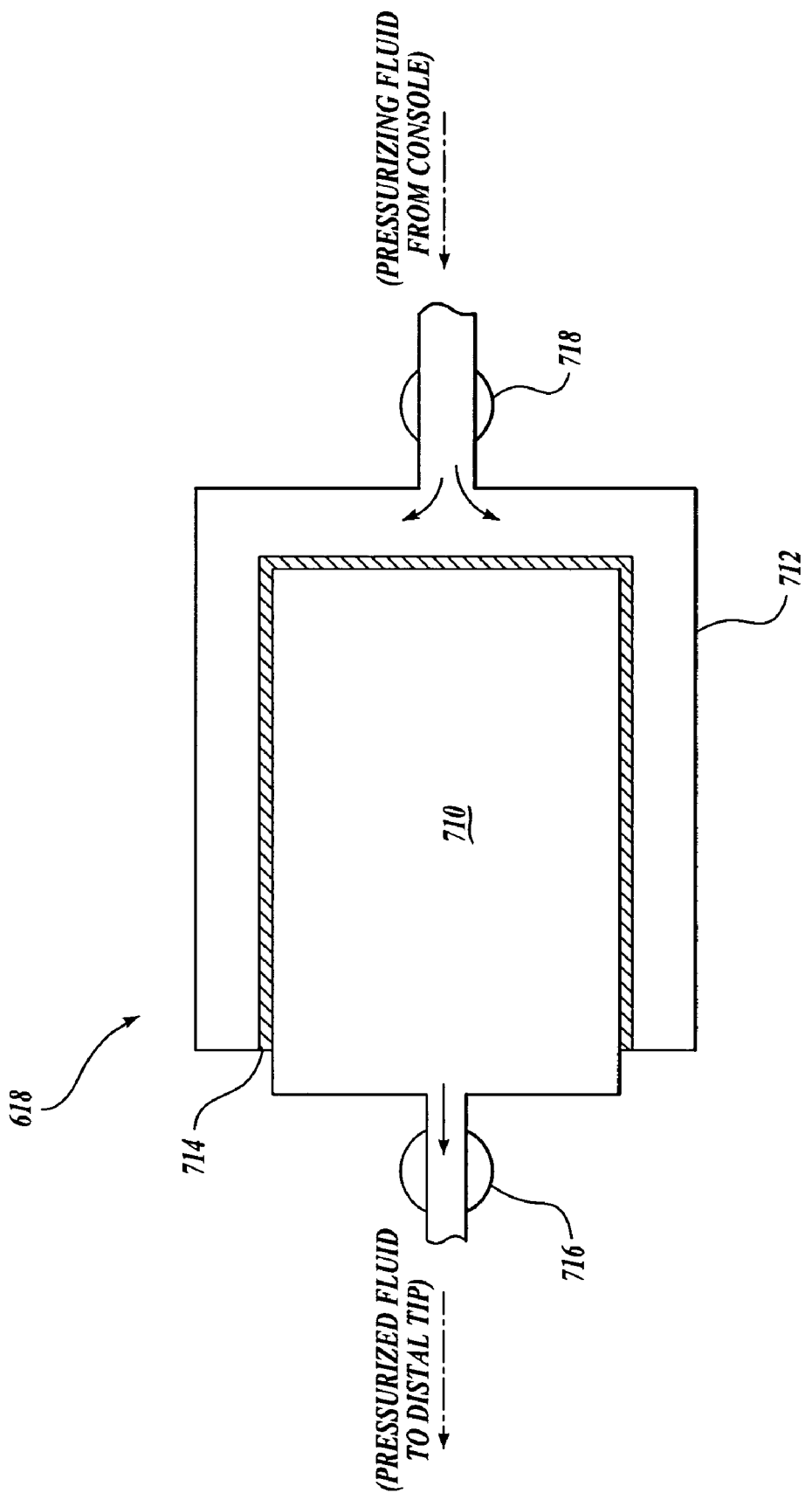
FIG. 7 illustrates a top view of the integrated fluid reservoir that is installed, optionally, within the handheld manual controller of FIG. 6 in accordance with an embodiment of the invention.

FIG. 7 illustrates a top view of an exemplary integrated fluid reservoir 618 that is installed, optionally, within handheld manual controller 116. Integrated fluid reservoir 618 includes a fluid bladder 710 surrounded on at least two opposite sides by a water bladder 712. The contacting surfaces between fluid bladder 710 and water bladder 712 are represented by a pressure interface 714. The combination of fluid bladder 710 and water bladder 712 that form integrated fluid reservoir 618 is installed into a recessed cavity within controller housing 610 of handheld manual controller 116.

Fluid bladder 710 is fluidly connected to a fluid channel that is fed into and along the full length of endoscope distal shaft 118 to endoscope distal tip 120. Fluid bladder 710 is in the form of a disposable, soft, flexible bladder that is easily detachable from within controller housing 610. Integrated fluid reservoir 618 includes a pinch valve 716 at the outlet of fluid bladder 710 to control the flow of fluid therefrom. Water bladder 712 is also in the form of a soft, flexible bladder; however, water bladder 712 is permanently installed within controller housing 610. Integrated fluid reservoir 618 includes a pinch valve 718 at the inlet/outlet of water bladder 712 to control the flow of fluid therethrough.

The capacity of liquid held within fluid bladder 710 is relatively small, compared with the capacity of fluid source 124 or fluid sources 410. Fluid bladder 710 may be sized, for example, to hold a small quantity of irrigation liquids, contrast media, medication, or dyes for marking tissue. An access door may be included within controller housing 610 of handheld manual controller 116 for installing or removing fluid bladder 710 as needed before, after, or during a medical procedure.

Integrated fluid reservoir 618 takes advantage of the supply of, for example, water passing through handheld manual controller 116 from, for example, fluid source 124 of the endoscopic system 100 or fluid sources 410 of the endoscopic systems 400 and 500. More specifically, the flow of water is able to pass in or out of water bladder 712 and, therefore, cause water bladder 712 to expand or contract. When water bladder 712 is expanded, pressure is created against fluid bladder 710 at the pressure interface 714. As a result, a pressure mechanism is created, and pressurized fluid is forced out of fluid bladder 710 and down the fluid channel of endoscope distal shaft 118 and delivered to endoscope distal tip 120. In operation, the user activates the pressure mechanism created by the combination of fluid bladder 710 and water bladder 712 via fluid activation button 620, which activates any associated pump and controls pinch valves 716 and 718 that enable the flow of, for example, water into water bladder 712 and fluid from fluid bladder 710.

Those skilled in the art will recognize that the method steps of method 300 may be adapted easily to apply to any of the various medical procedures that use various types of fluid sources, such as shown in FIGS. 1 through 7. For example, fluid source 124, fluid reservoir 130, fluid sources 410, and integrated fluid reservoir 618, as described in reference to the endoscopic systems 100, 400, and 500 of the present invention, provide the user with the flexibility of changing fluids either in advance of a procedure or on-the-fly as needed, instead of relying on fixed fluid sources only. Furthermore, the arrangement of fluid sources, pumps, and valves within the endoscopic systems 100, 400, and 500 of the present invention provide a controlled fluid delivery rate and a controlled way of mixing fluids.

Figure 8:
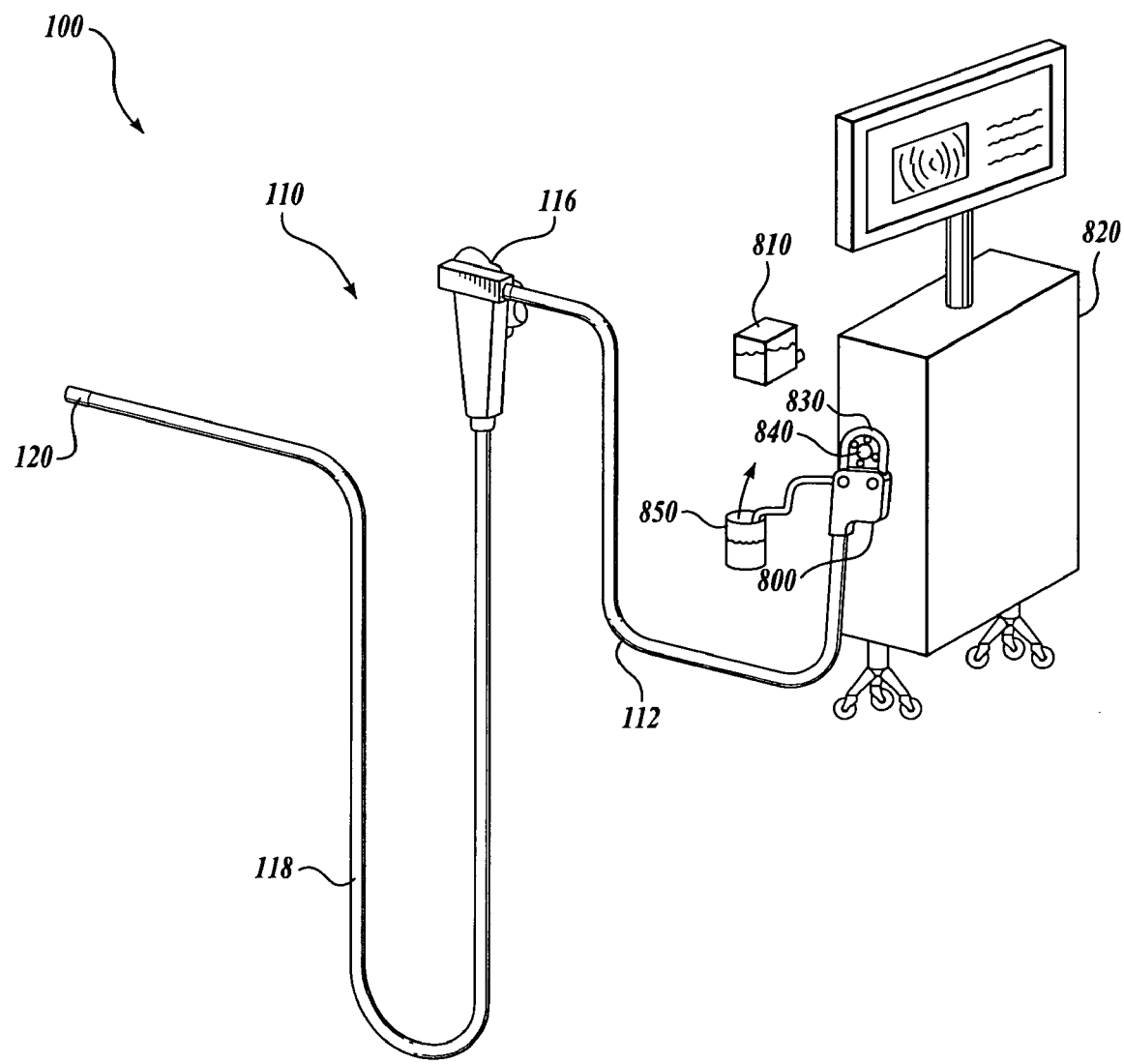
FIG. 8 illustrates a single use endoscope having a proximal connector positioned on a reusable control unit in accordance with one embodiment of the present invention.

FIG. 8 shows yet another alternative embodiment of a fluid delivery system for an endoscope. An endoscopic system 100 includes an imaging endoscope 110 having a handheld manual controller 116 that is used by the physician to operate the endoscope and to steer the endoscope distal tip 120. The proximal end of the endoscope includes a connector 800 that is releasably secured to a reusable console 820. As will be described in further detail below, the connector 800 supplies liquids to various lumens in the endoscope in order to perform such functions as bolus wash, jet wash, lens wash, as well as providing vacuum and insufflation. The connector 800 is fluidly coupled to a reservoir 810 including a liquid such as water or saline for delivery to the patient. The connector 800 also includes a U-shaped loop of tubing 830 which engages the rollers of a peristaltic pump 840 for providing fluid pressure to the liquid in the reservoir 810 such that it can be selectively delivered to the lumens of endoscope to perform the desired tasks. The connector 800 is also connected via a tube to a vacuum collection jar 850 that captures retrieved aspirated liquids, debris, tissue samples, etc., from the endoscope.

Figure 9A:
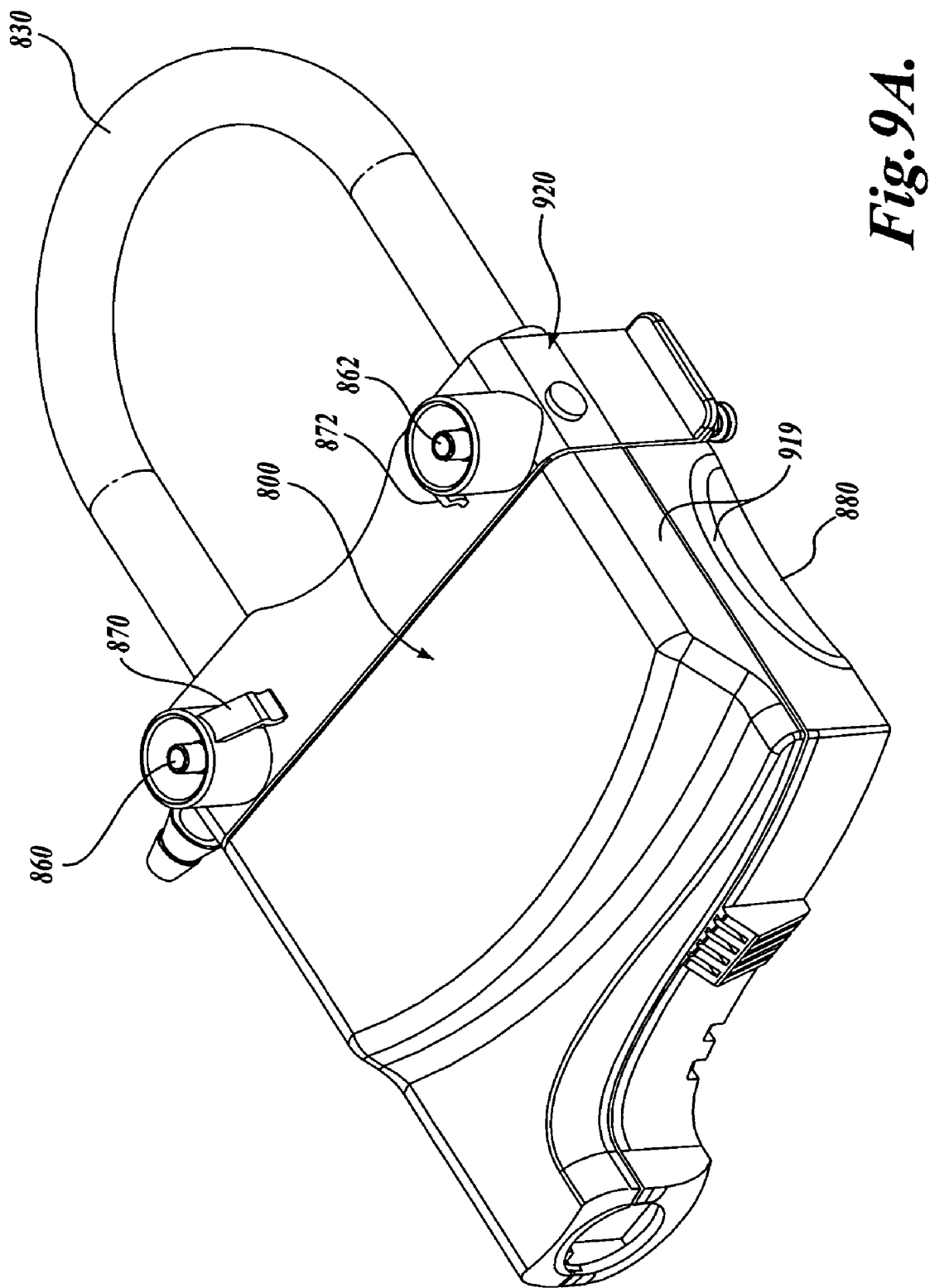
FIGS. 9A and 9B illustrate further details of a proximal connector.
Figure 9B:
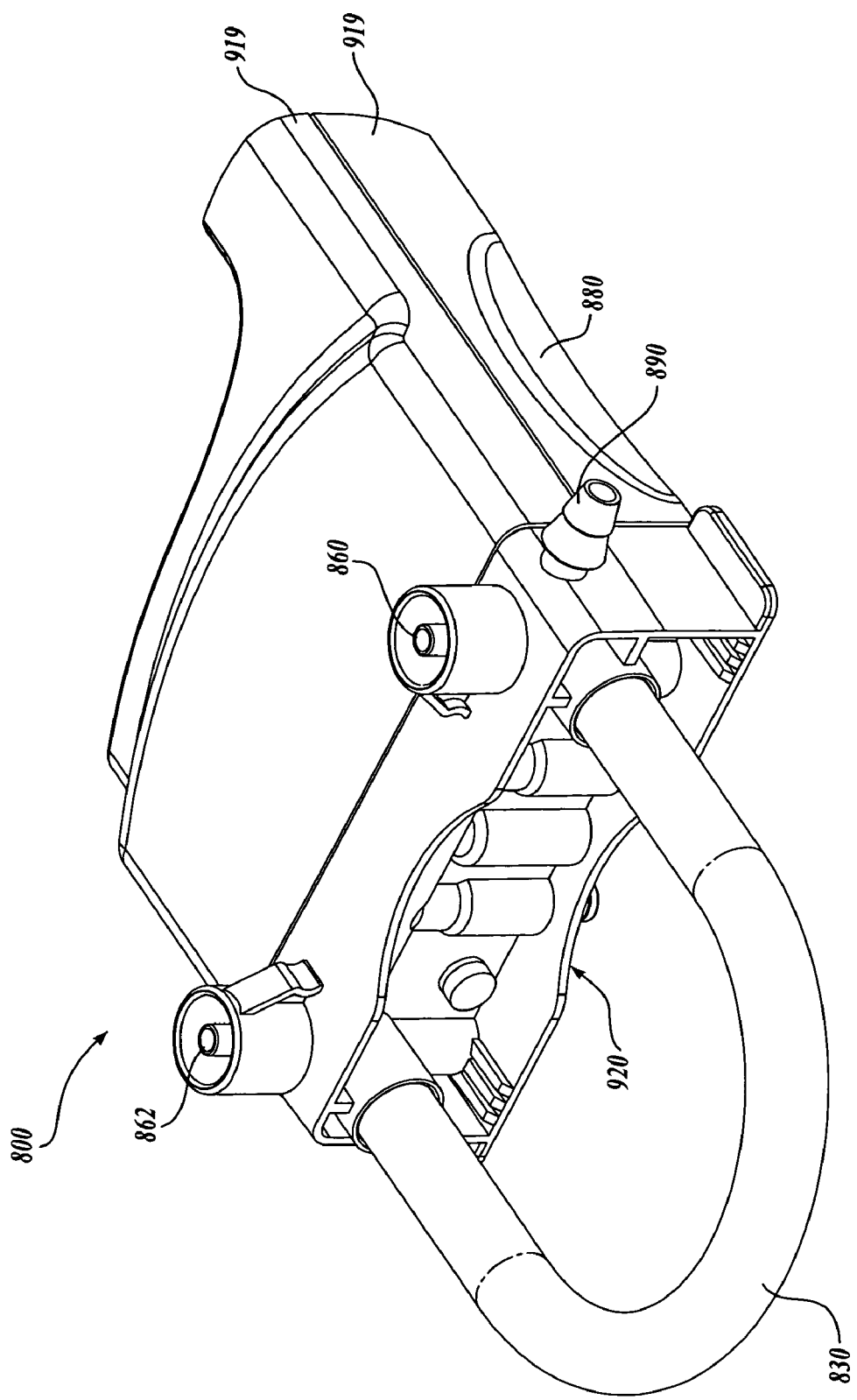

FIGS. 9A, 9B and 9C illustrate further detail of one embodiment of the proximal connector 800. In the example shown, the connector 800 is made from a molded housing having front and rear halves 919 that are joined to a molded fluid manifold 920. The connector 800 is sufficiently inexpensive to manufacture that it can be a disposable item. However, the connector design could also be made to withstand repeated disinfection procedures that are performed with reusable endoscopes.

As shown in FIG. 9A, the proximal connector 800 includes a pair of ports 860, 862 that receive water from and return water to the fluid reservoir 810 shown diagrammatically in FIG. 8 and in much greater detail below. The reservoir is secured to the ports 860, 862 with a pair of retaining detents 870, 872 that engage cooperating elements on the reservoir. The proximal connector 800 also includes one or more ergonomic hand grip depressions 880 that facilitate the manual insertion and removal of the proximal connector 800 from the console 820. As shown in FIG. 9B, the proximal connector 800 includes a vacuum port 890 that is connected by a tubing to the vacuum collection jar or trap (850, shown diagrammatically in FIG. 8). The U-shaped tubing section 830 receives fluid from the fluid input port 860 and delivers it under pressure to a fluid manifold tube within the connector.

The rear surface of the connector 800 is shown in FIG. 9C. This view shows the countersunk fasteners 904 that hold the halves 919 together. The rear surface includes one or more sockets and/or fluid connections 900, 902 that are received on corresponding guide pegs and/or cooperating fittings on the console (or the interface between proximal connector and console described below) in order to aid in the placement of the proximal connector on the console. In addition, the proximal connector 800 also includes a number of reciprocating valve pistons or spools 910, 912, 914, 916 that are selectively actuated by electromagnetic, hydraulic, pneumatic, or other console-mounted actuator types in order to direct fluids within the manifold 920 to various lumens in the endoscope. An electrical connector 929 is seated within an outwardly extending rim 932 on the rear surface of the proximal connector 800. The connector 929 serves to connect electrical components within the endoscope to a mating electrical connector on the console.

FIG. 10A illustrates some of the internal components of the proximal connector 800. The proximal connector includes the manifold member 920 which can have a number of ports 922, 924, 926 that are activated by movement of the valve spools to selectively deliver pressurized liquid from the reservoir, through the manifold, to various lumens of the endoscope. In the embodiment shown, port 922 delivers liquid for the bolus wash in the endoscope, port 924 delivers liquid for a lens wash and a port 926 delivers liquid for a jet wash.

The proximal end of the endoscope intermediate shaft 112 (FIG. 8) fits within a receiving portion 940 of the proximal connector 800. The receiving portion 940 includes a number of ribs 950 that retain the proximal end of the shaft such that it cannot be easily pulled from the connector 800. In one embodiment, the receiving portion includes an anti-rotation boss 952 that extends through a hole in the endoscope shaft such that the shaft cannot be rotated within the connector.

Figure 10B:
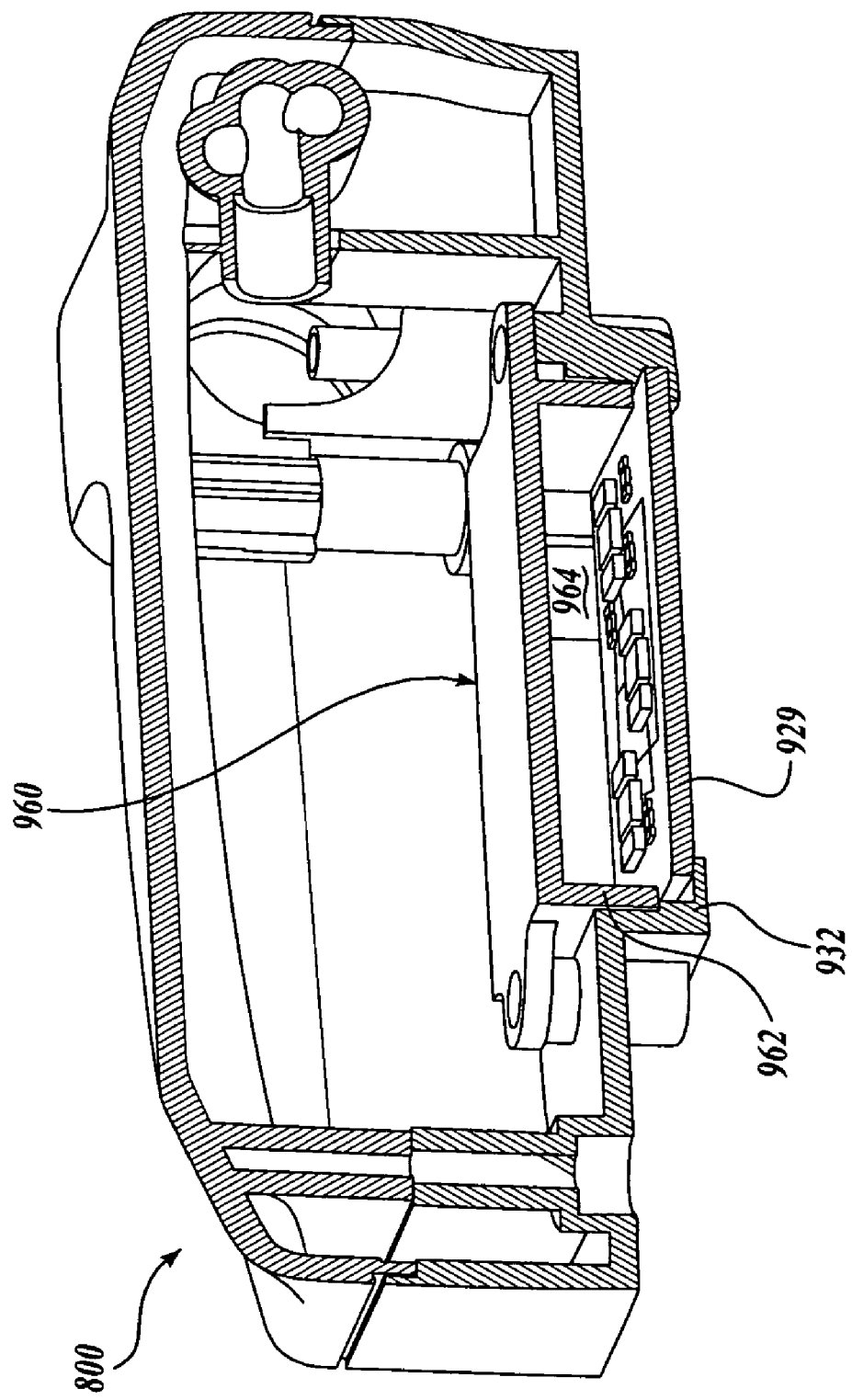
FIG. 10B illustrates a circuit board retaining feature of the proximal connector in accordance with an embodiment of the present invention.

With reference to FIG. 10B, a cover 960 is placed over the inner surface of electrical connector 929 to secure it in the rear surface of the proximal connector. Cover 960 also acts as a splash guard. The circuit board 929 is held to the rear surface of the connector 800 behind a lip of the outwardly extending rim 932 on the rear surface of the connector 800. The rim has an opening that exposes the contacts on the connector and a lip that is sized to be smaller than the connector 929. The cover 960 has an outwardly extending rim 962 that fits within the rim 932 in order to compress the circuit board against the inside surface of the outer rim 932 when the cover 960 is secured to the rear surface of the proximal connector 800.

Returning to FIG. 10A, a series of molded channels 970 operate to guide the various tubes or lumens in the endoscope to the ports 922, 924, and 926 that provide fluids to the endoscope as well as a tube that it is connected to. A port 930 provides insufflation gas to the endoscope (with reference to FIG. 9C, socket 902 receives the insufflation fitting, as compared to socket 900 which receives a larger locating boss).

Again referring to FIG. 10A, the proximal connector 800 also includes a four-way fitting 980. Fitting 980 can direct fluids and air/vacuum to the working channel lumen within the endoscope shaft. Fitting 980 includes a port 982 that is oriented generally in line with the endoscope shaft and is connected to a working channel lumen of the endoscope. A port 984 extends in a direction perpendicular to the port 982 and in the embodiment shown is connected via a tube to the port 922 that supplies water for a bolus wash.

Figure 10C:
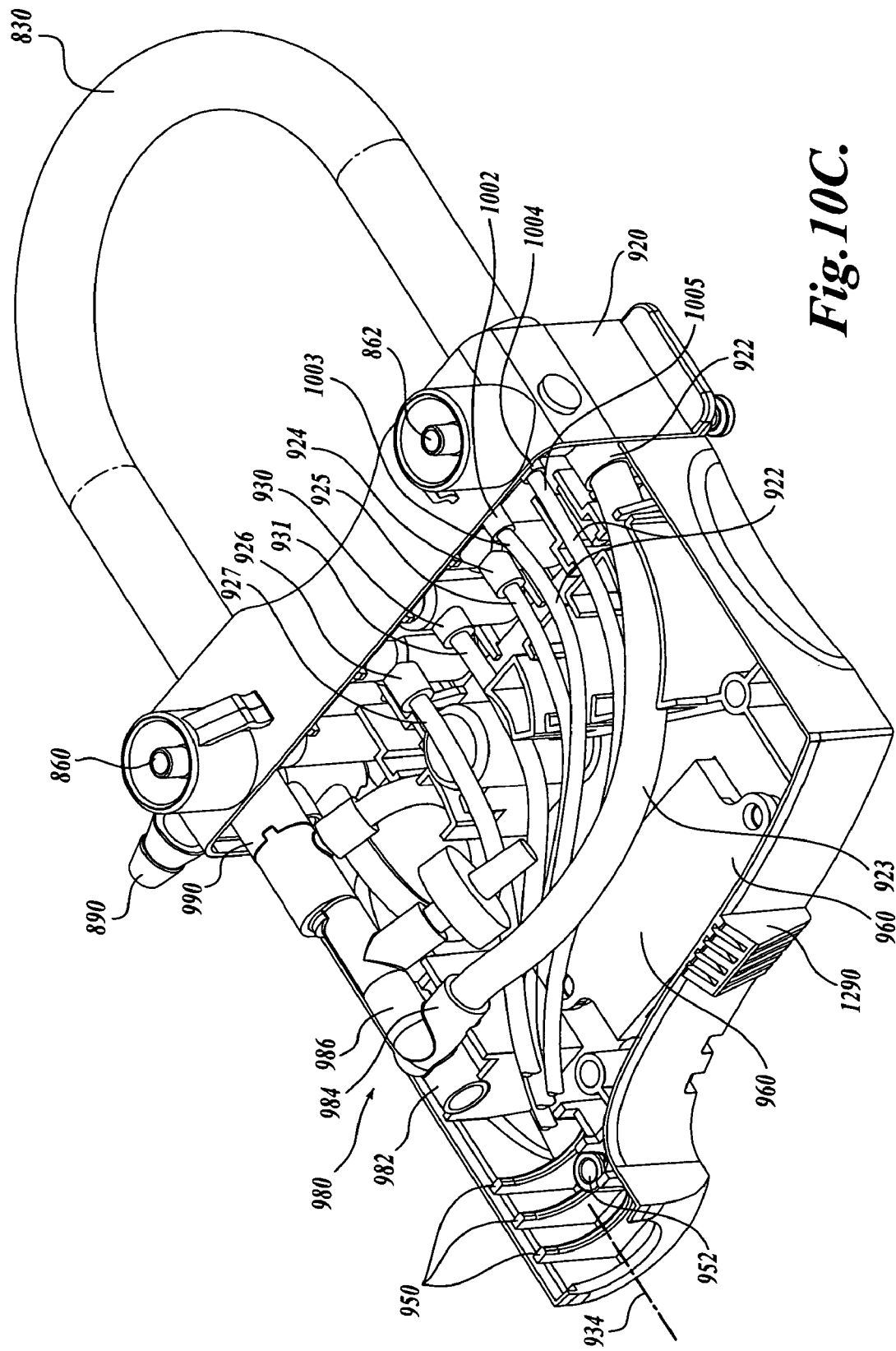
FIG. 10C illustrates a cutaway view similar to FIG. 10A but with additional parts shown.

A port 986 is generally in line with the port 982 and is fluidly coupled by a tube to a bolus wash overpressure valve 990 and an air bleed assembly as will be explained in further detail below. In addition, the fitting 980 includes a fourth port positioned in line with the working channel and beneath the port 986 that is coupled by a tube to a vacuum port below valve 990. The arrangement of these lines is shown in FIG. 10C. Port 922 (at the right) for the bolus wash is connected to fitting port 984 (at the left) by a tube 923. Port 924 (lens wash) connects to and through the endoscope proximal shaft by a tube 925. Similarly, a tube 927 leads from the port 926 (et wash) and a tube 931 leads from the port 930 (insufflation) into and through the endoscope proximal shaft. Ports 922, 924 and 926 communicate with the common manifold whereas port 930 does not. Ports 1002, 1004 and corresponding tubes 1003, 1005 can be configured to supply a cooling flow of liquid to the endoscope LEDs or other heat generating components. A wiring harness (represented by broken line 934) also extends along or through the endoscope shaft and connects to the electrical connector below the cover 960.

Figure 11A:
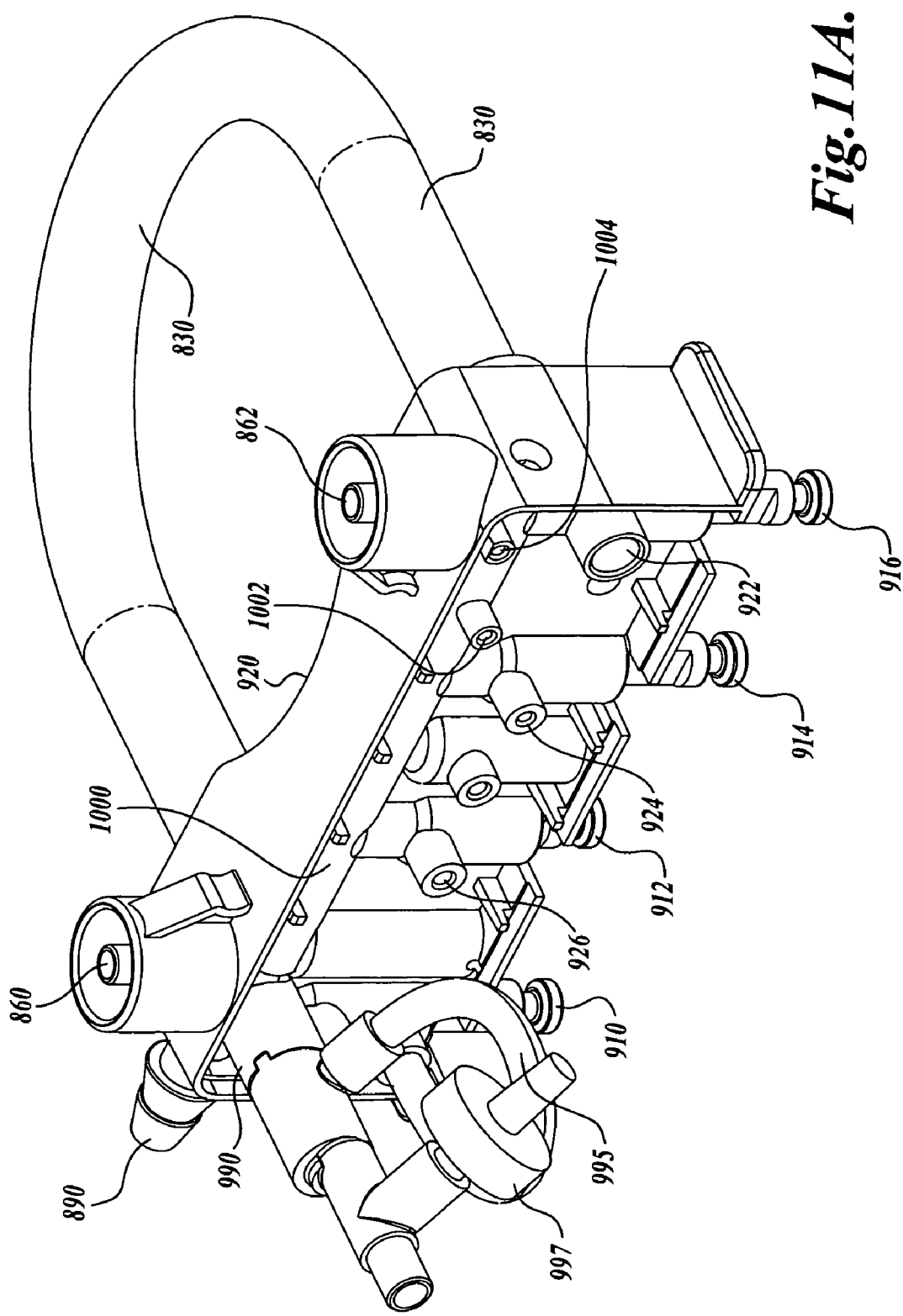

FIGS. 11A, 11B and 11C illustrate further detail of the manifold 920 within the proximal connector. In the embodiment shown, the manifold is molded as a separate piece and is joined to the front and rear halves of the proximal connector 800. The manifold 920 includes a common tube or channel 1000 which is fluidly connected to each of the ports 922, 924 and 926. In addition, the tube 1000 includes the port 1002 that continually delivers a cooling liquid through a lumen to a heat exchanger within the distal tip of the endoscope in order to cool the illumination devices. In addition, the manifold 920 includes a port 1004 which receives the cooling liquid back from the heat exchanger and supplies it to the port 862 for return to the liquid reservoir. The corresponding tubes 1003 and 1005 are seen in FIG. 10C.

Other aspects of the tube routing through the manifold component are best seen in FIG. 11B. Vacuum port 1050 connects to the bottom port of the four-way fitting 980 (fitting 980 is seen, for example, in FIGS. 10A and 10C) below port 986. A pressure control loop tube 993 connects between a bottom manifold vacuum port 995 and the upper valve 990. An upper bleed control check valve 997 connects to the vacuum tube on the distal side of valve 990. Operation of the vacuum system is described in more detail below.

FIG. 11C illustrates how the U-shaped flexible tubing 830 is secured within two ports 832, 834 on the top of the manifold. The port 832 is fluidly coupled to the port 860 that receives liquid from the fluid reservoir. The port 834 is fluidly coupled to the tube 1000 in the manifold 920. The tubing 830 is preferably made of propylene or other flexible material that can be pressurized by the rollers of the pump wheel for the peristaltic pump on the console.

Figure 12:
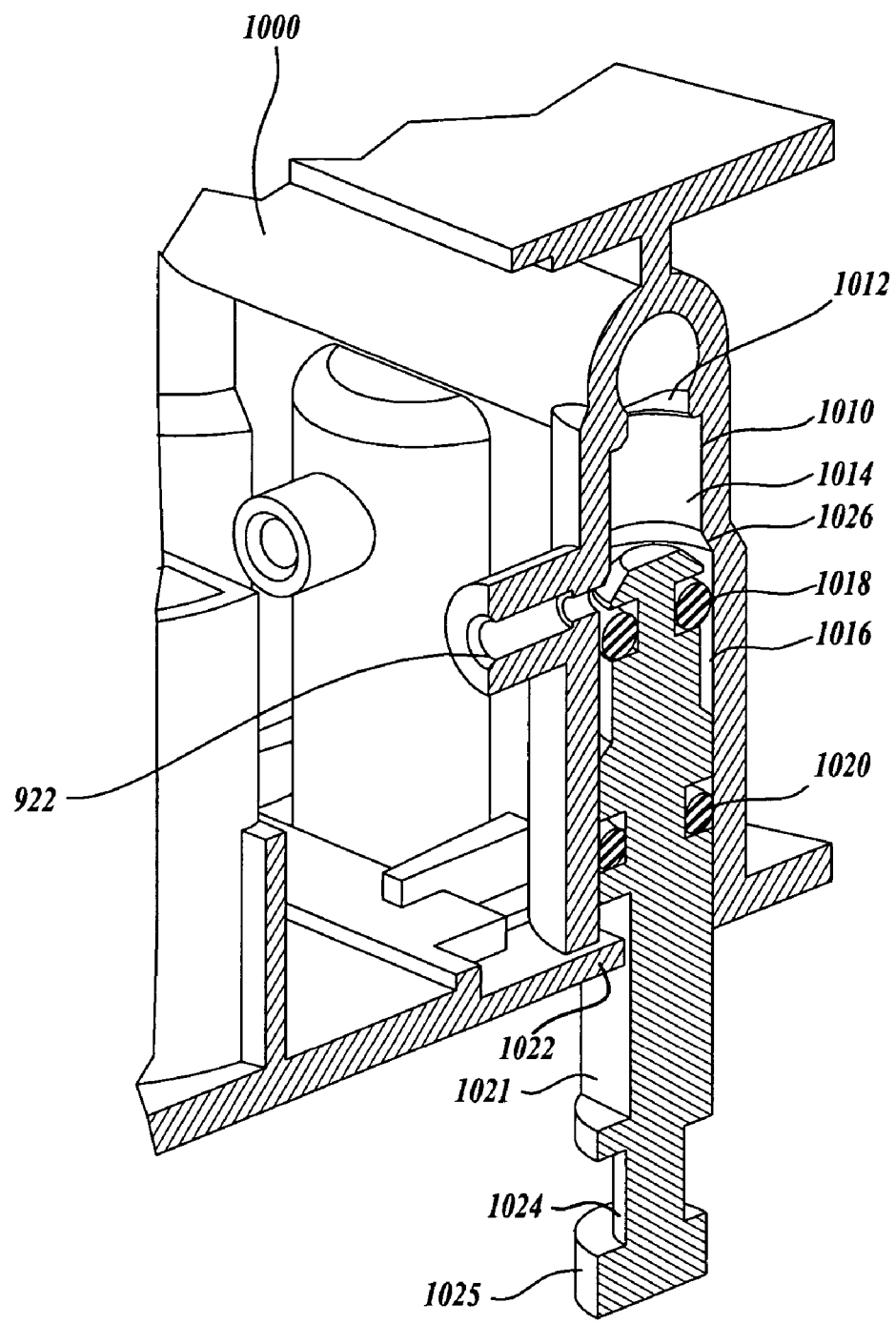
FIG. 12 illustrates a valve spool within a manifold in accordance with an embodiment of the present invention.

FIG. 12 illustrates further detail of the valve pistons or spools within the ports connected to the manifold. As indicated above, the manifold includes a tube 1000 that contains a pressurized liquid to deliver to each of various liquid ports. In each of the liquid ports, for example, port 922, liquid within the tube 1000 flows through a cylindrical chamber 1010 having an opening 1012 that fluidly connects the chamber 1010 with the tube 1000. Chamber 1010 has a first diameter in the space between the port 922 and the tube 1000 and a larger diameter in a region 1016 occupying the remainder of the chamber. A generally cylindrical valve piston or spool, such as valve spool 916, is slidably received within the valve chamber 1010. The valve spool includes a pair of longitudinal spaced O-rings 1018, 1020. O-ring 1018 has a smaller diameter that is for reception within the smaller diameter section 1014 of the chamber 1010. Moving the O-ring 1018 into the smaller diameter section 1014 seals the port 922 from receiving fluids from the tube 1000. Conversely, retracting the valve spool in the chamber 1010 creates a fluid path between the tube 1000 and the port 922 when the O-ring 1018 is below the port 922 (the position shown in FIG. 12). At the transition of the larger and smaller diameters of the valve chamber, the chamber is chamfered at an area 1026 to prevent the O-ring 1018 from becoming sheared as the valve spool assembly is moved back and forth. In one embodiment of the invention, the chamfer is set at approximately 30 degrees.

The valve spool also includes a notched section 1021 in which a corresponding tab 1022 from the rear half of the proximal connector is fitted thereby retaining the valve spool in the manifold 920 and limiting the range of motion of the spool. Finally, the valve spool includes a stepped neck portion 1024 of a smaller diameter that allows the spool to be grasped at the enlarged head 1025 by a console-mounted actuator to move the valve spool in and out to close and open the valve.

Figure 13A:
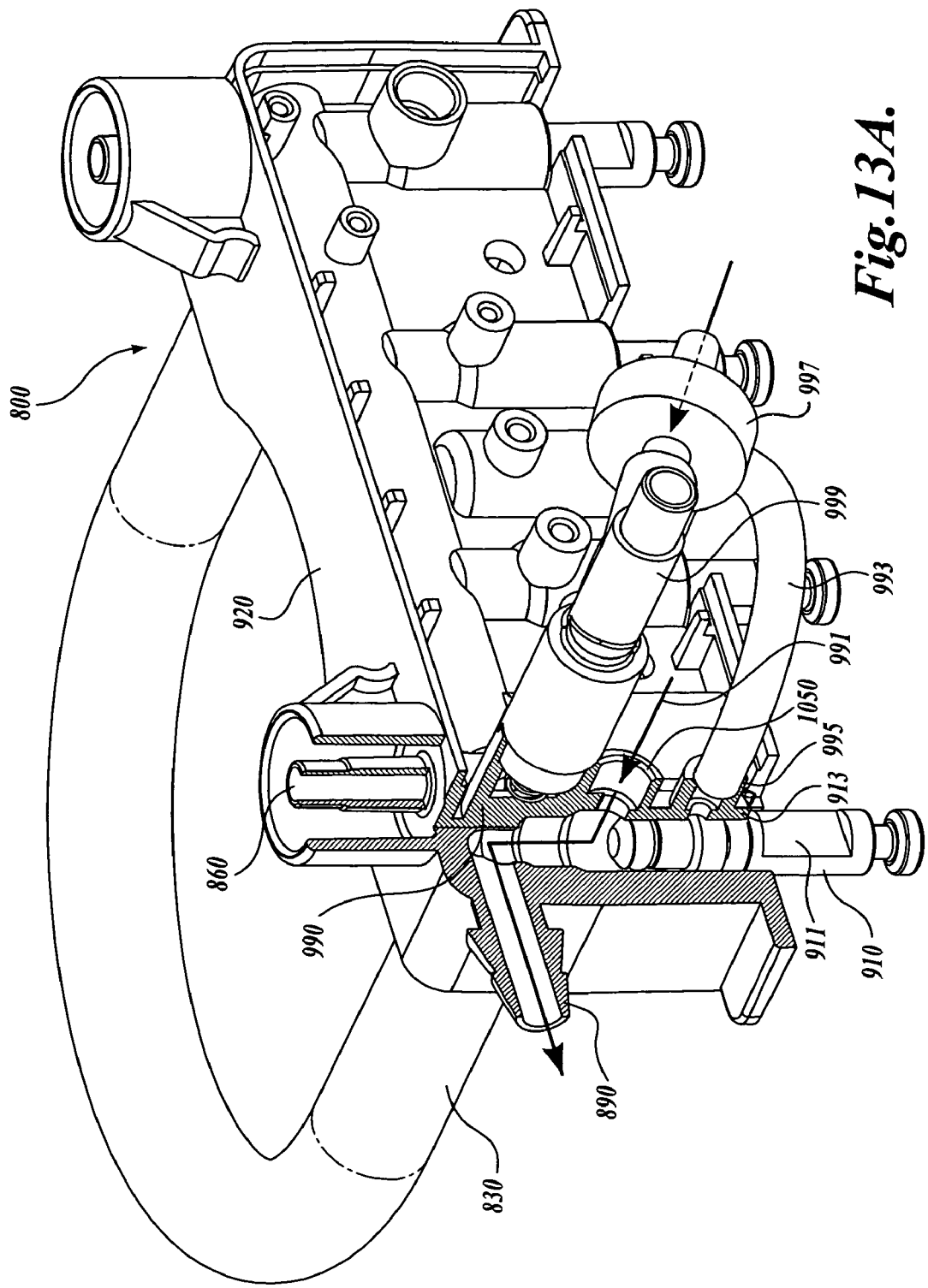
FIGS. 13A and 13B illustrate a vacuum line and valve within a manifold in accordance with an embodiment of the present invention.
Figure 13B:
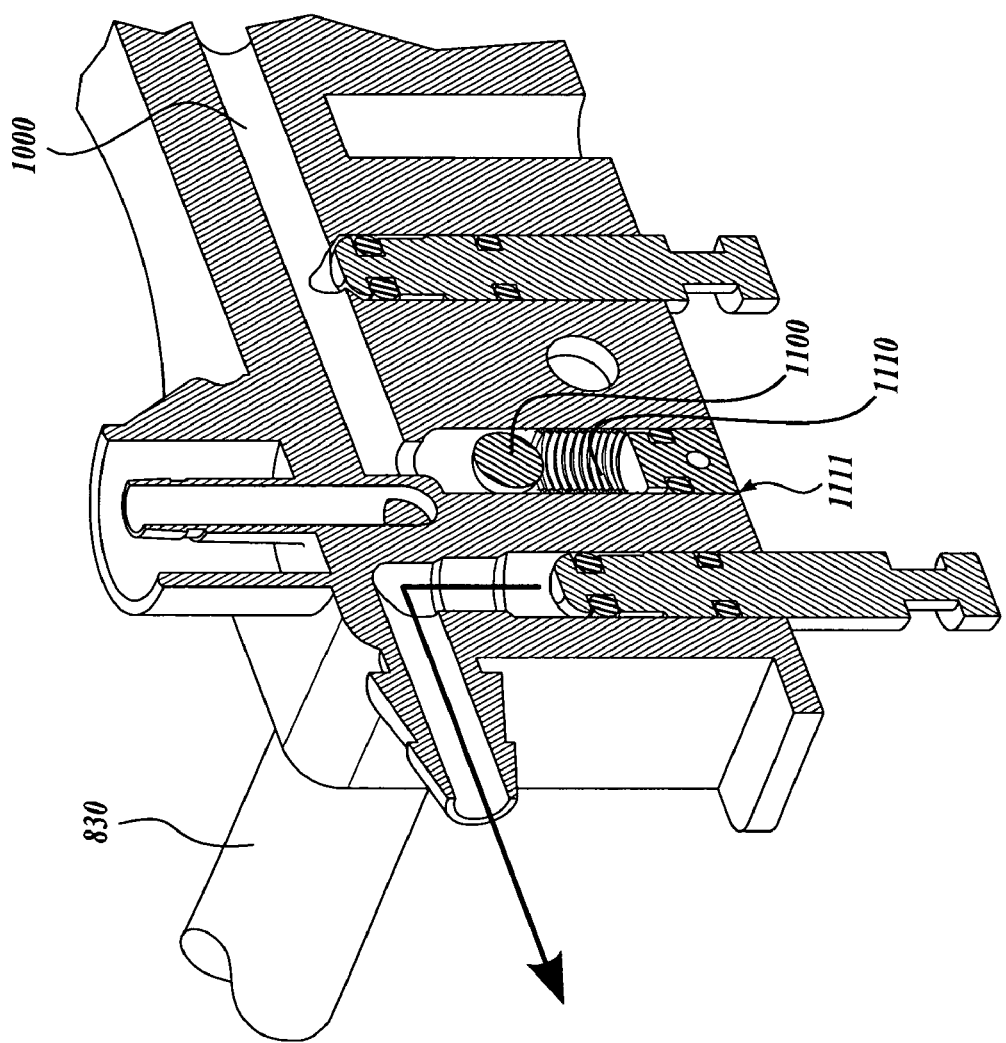

FIGS. 13A and 13B illustrate the vacuum valve assembly within the manifold. The vacuum assembly includes a vacuum port 1050 that is connected by a tube to a port on the four-way fitting 980 that is generally in line with the working channel lumen of the endoscope. The valve assembly includes a valve piston or spool 910 having a construction similar to that described above, which is selectively moved by an actuator to provide fluid communication between the vacuum port 1050 and the port 890 that is coupled to the vacuum collection jar or trap and house vacuum source or another vacuum source. FIG. 13A also shows the low pressure bolus wash bypass port 990 that is fluidly connected to the vacuum port 890. If a bolus wash is applied while the physician has a tool in the working channel or while the working channel is blocked, liquid supplied from the manifold will open a valve in the low pressure bolus wash bypass port 990. By entering the bypass port 990, the working channel is prevented from becoming pressurized with a liquid that may splash onto a physician or assistant.

Figure 14:
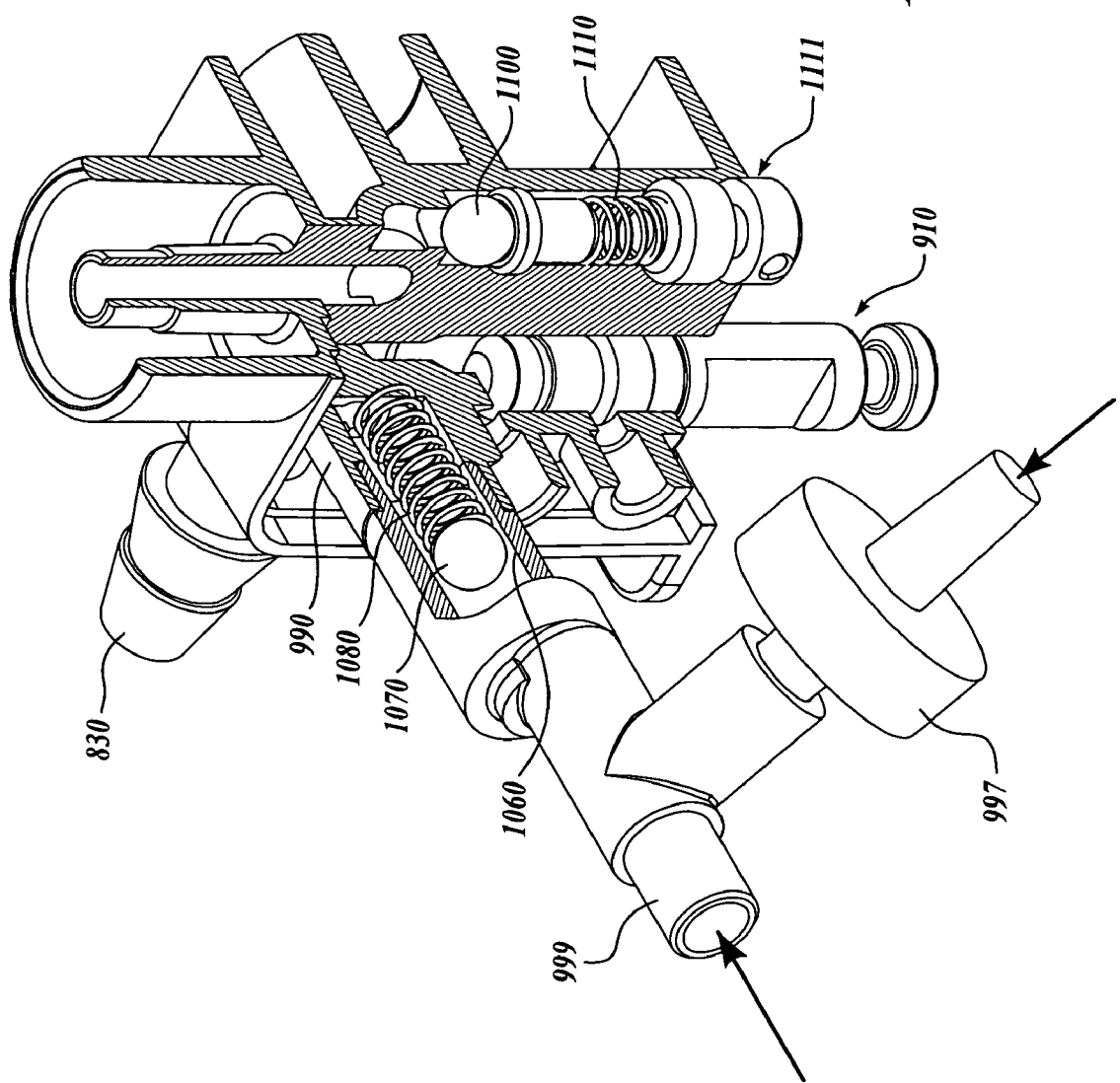
FIG. 14 illustrates a pressure relief valve within a manifold in accordance with an embodiment of the present invention.

Further detail of the low pressure bolus wash bypass valve is shown in FIG. 14. The bypass port 990 includes an insert 1060 that secures a ball valve 1070 and biasing spring 1080 in the port 990. The insert 1060 has a lip that mates with the surface of the ball valve 1070 in the port 990 by virtue of pressure from the spring 1080. Once the pressure of the bolus wash liquid in the port 990 overcomes the spring force of the spring 1080, the ball valve 1070 is opened thereby allowing passage of liquid through the insert 1060 and port 990 to the vacuum port 890. Also shown in FIGS. 13B and 14, the manifold also includes a high pressure bypass valve 1111 including a ball valve 1100 and spring 1110 that operate to relieve pressure in the manifold tube 1000. If pressure within the tube 1000 exceeds the spring force of the spring 1110, ball valve 1100 is forced open thereby opening a fluid channel between the manifold tube 1000 and the low pressure side of the tubing 830. In some embodiments of the invention, it may be necessary to employ a metal seating ring within the cylinder of the high pressure bypass valve in order to provide proper mating seal between the cylinder and the ball valve 1100.

The vacuum system allows liquids and solid material, including polyps, to be aspirated through the endoscope and the manifold piece 920 of the proximal connector 800. In FIG. 13A, valve piston or spool 910 is shown in the "open" position in which maximum aspiration is provided through the port 1050 in the direction of the arrow 991, up through the manifold piece to the suction outlet 890. The aspiration (vacuum) system provides two additional features. Check valve 997 provides for a small bleeding air flow from the atmosphere into the upper tube 999 which, in turn, is connected back to the vacuum port by way of the four-way connector described above. In some scenarios, the distal tip of the endoscope will stick to the lining of the large intestine sufficiently that vacuum is maintained when the vacuum valve 910 is closed. Check valve 997 allows the aspiration channel to return to atmospheric pressure for easy removal of the distal tip of the endoscope from the lining. The bleed bypass tube 993 provides another feature. In the open condition, for maximum aspiration, shown in FIG. 13A, the bleed tube 993 and port 995 are sealed from the aspiration channel which leads to the vacuum port 890. However, the notched portion 911 of the vacuum valve and the inner face 913 of port 995 are configured such that, when the valve is closed, there is some small air communication from outside the valve to the bleed tube 993, and from there into the endoscope working channel. This prevents the full force of the house vacuum from being instantaneously drawn upon opening of the valve. Rather, the vacuum ramps up when the valve is opened, based on the bleed permitted when the valve is closed.

Figure 15:
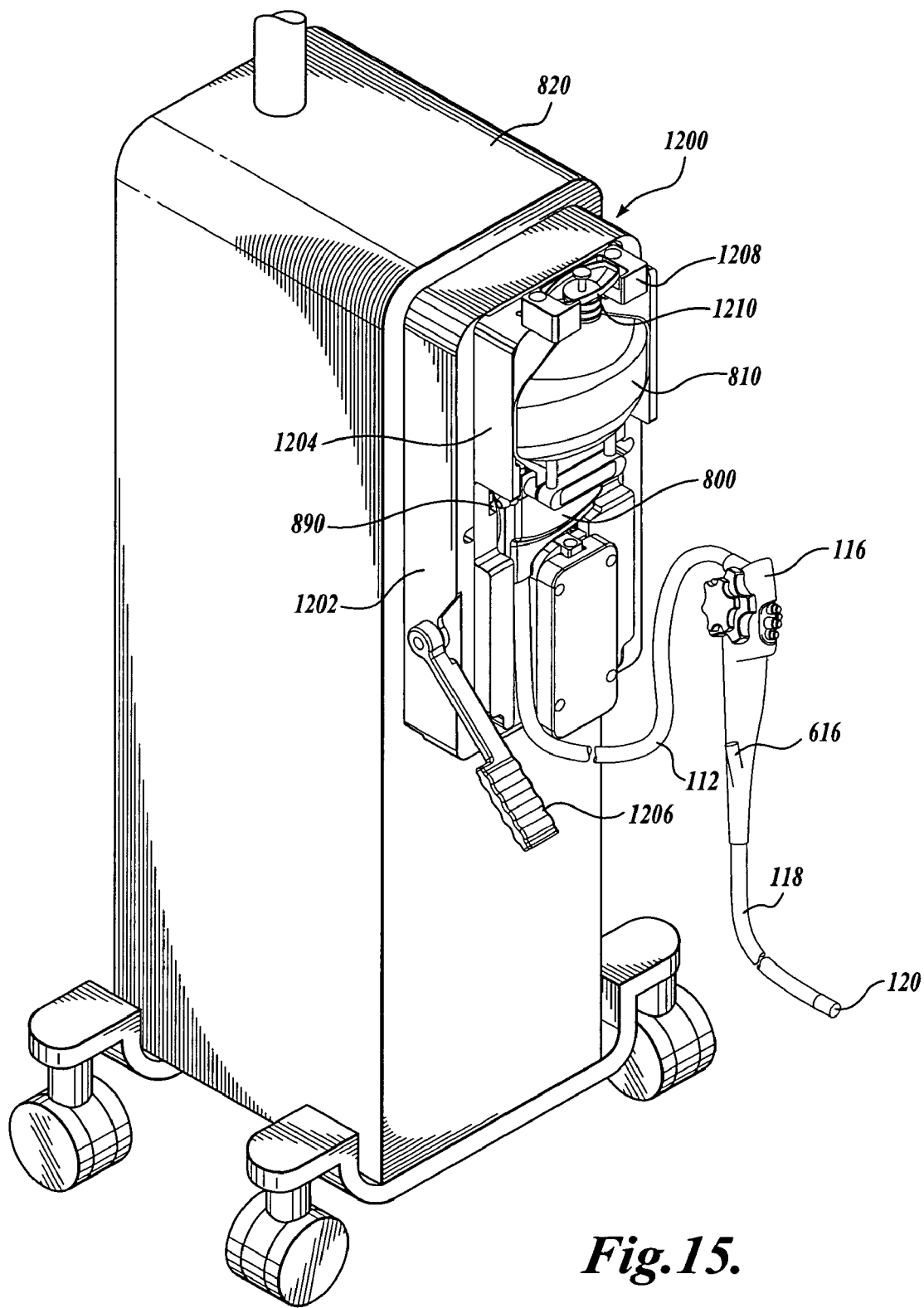
FIG. 15 is a top perspective illustrating attachment of a proximal connector of the type shown in FIGS. 9-14 to a console of an endoscope.

FIGS. 15-27 show more detailed aspects of the attachment of the proximal connector 800 to the console 820, although these views are still somewhat diagrammatic and have part sizes exaggerated for ease of description. With reference to FIG. 15, to orient the parts, the endoscope distal end 120 is connected by a distal shaft section 118 to the hand controller 116. Controller 116 is connected to the proximal connector 800, of the type described with reference to FIGS. 9-14, by the proximate endoscope shaft section 112. Knobs and buttons on the controller 116 provide for articulation of the endoscope distal end portion and control of illumination, bolus wash, high pressure wash, and so on. The handheld controller 116 also has the working channel access port 16, shown diagrammatically, by means of which probes, tools, and so on, may be introduced into the working channel of the endoscope. The proximal connector 800 attaches to the console 820 by way of an interface 1200 which includes a first interface plate 1202 and a sliding plate 1204 that moves up and down relative to plate 1202 by manipulation of a swinging handle 1206. The sliding plate 1204 has a top mount 1208 for the cap portion 1210 of a liquid reservoir 810. Such reservoir hangs from the mount 1208 and is attached at the bottom to the proximal connector 800. In general, with the handle 1206 swung upward to a first receiving position such that the sliding plate 1204 is in a vertically raised position, the proximal connector 800 is manually fitted onto the sliding plate, and the reservoir 1212 is connected. The sliding plate forms a recess or socket of the approximate size and shape of the periphery of the body of the proximal connector 800. As described in detail below, swinging of the handle 1206 downward shifts the sliding plate 1204 downward to a second operating position and secures the various valve pistons or spools to console-mounted actuators.

Figure 16:
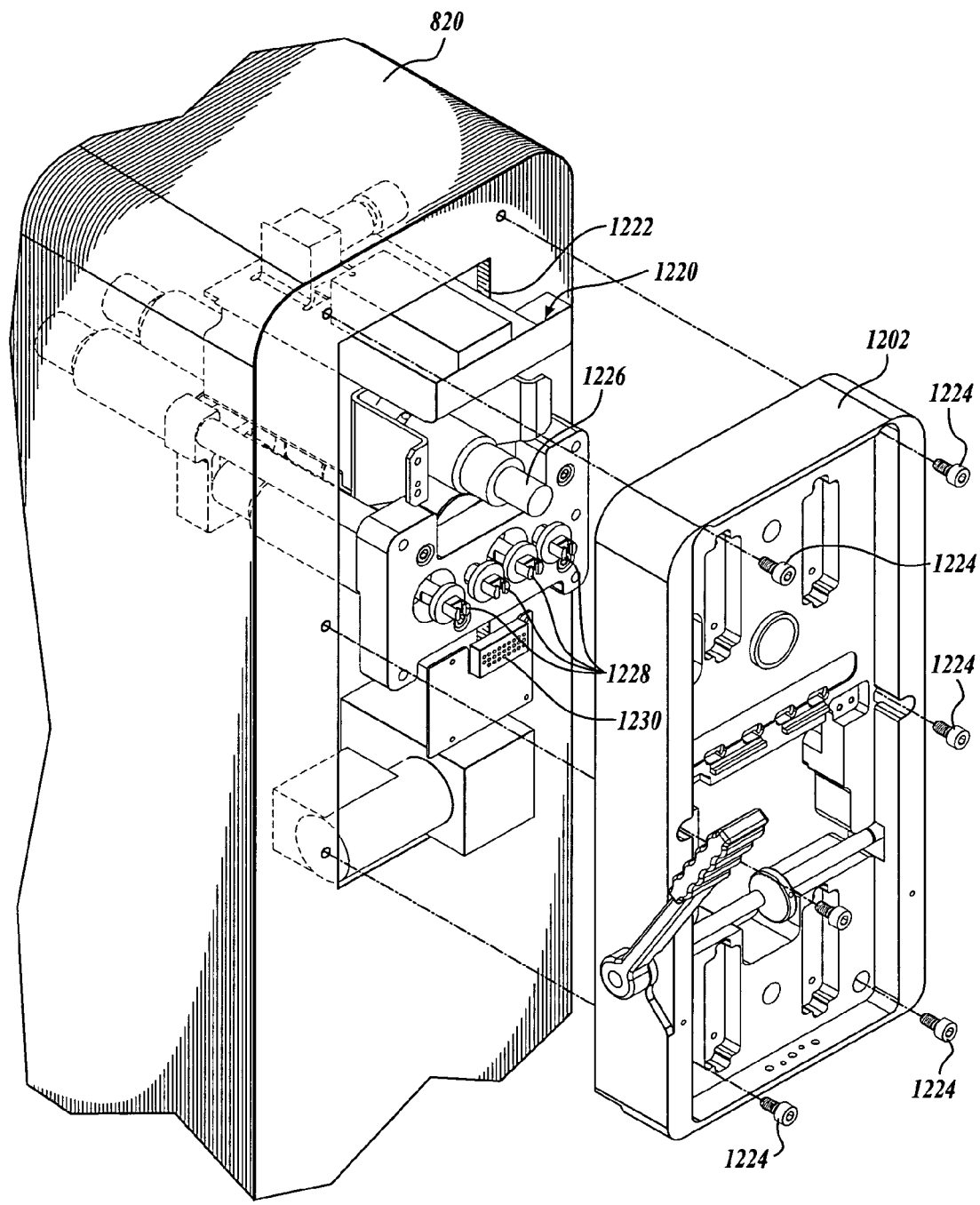
FIG. 16 is a fragmentary top perspective of a portion of the console of FIG. 15 with parts shown in exploded relationship.
Figure 17:
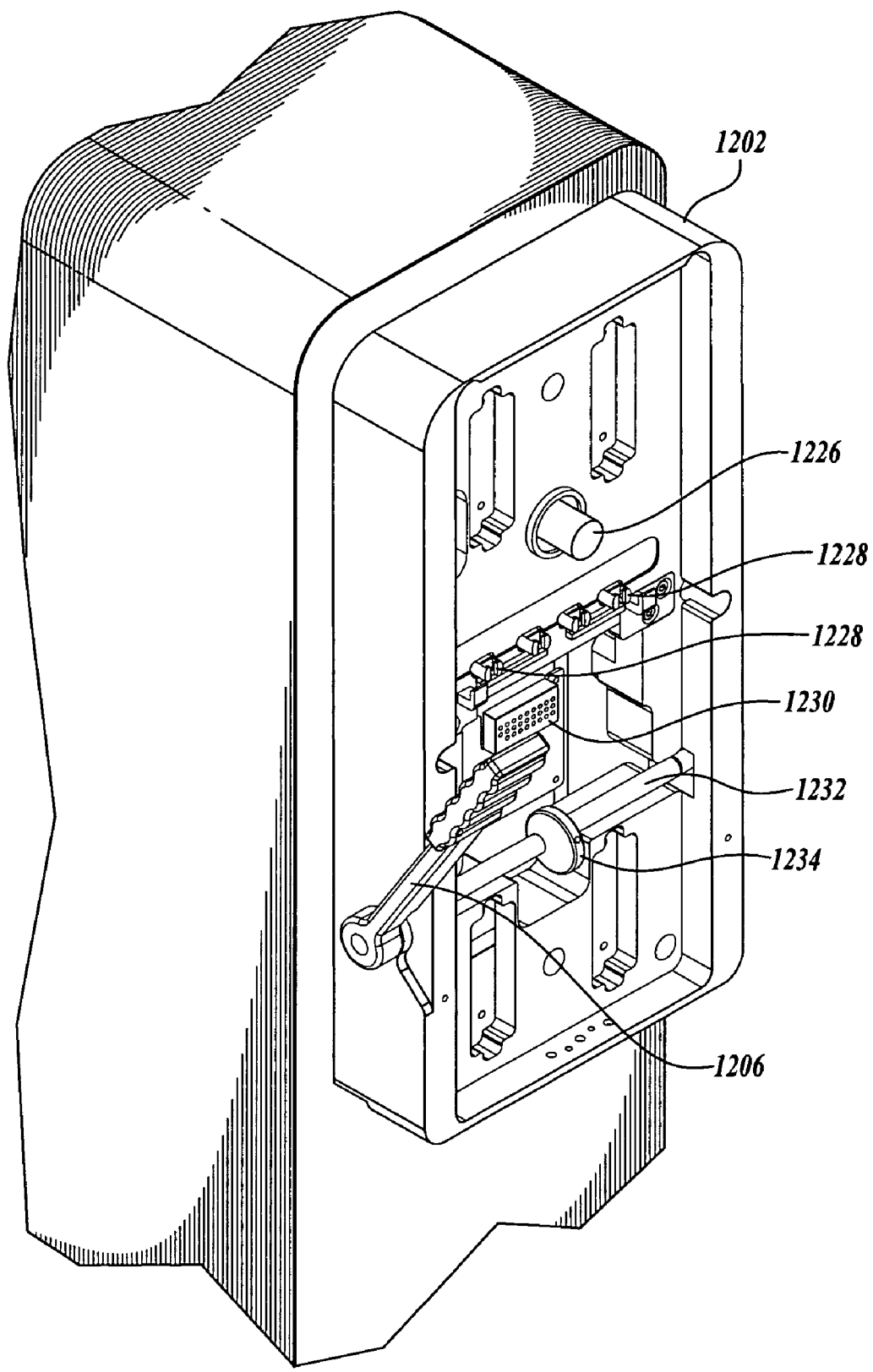
FIG. 17 is a corresponding top perspective with parts assembled.

With reference to FIG. 16 (parts shown exploded) and FIG. 17 (parts shown assembled), the stationary interface plate 1202 is secured to a pump and valve actuator assembly 1220. Plate 1202 and assembly 1220 are slid rearward into a cavity 1222 of the console 820 and secured by fasteners 1224. Assembly 1220 includes the rotary shaft 1226 for the peristaltic pump, as well as end effectors 1228 (from solenoids, for example) for the proximal connector valves. In the assembled condition shown in FIG. 17, the pump shaft 1226 is exposed and protrudes from the interface plate 1202. Similarly, the reciprocating end effectors 1228 extend through holes or slots of the plate 1202 so that there is no interference with reciprocating movement that ultimately controls opening and closing of the valves. Plate 1202 also has an opening for the electrical connector 1230.

The swinging lever 1206 connects to a transverse shaft 1232 having a projecting cam lobe 1234 at about its center. Up and down swinging movement of the lever 1206 rotates the horizontal shaft and the cam lobe such that the cam moves down when the lever moves down and up when the lever moves up.

Figure 18:
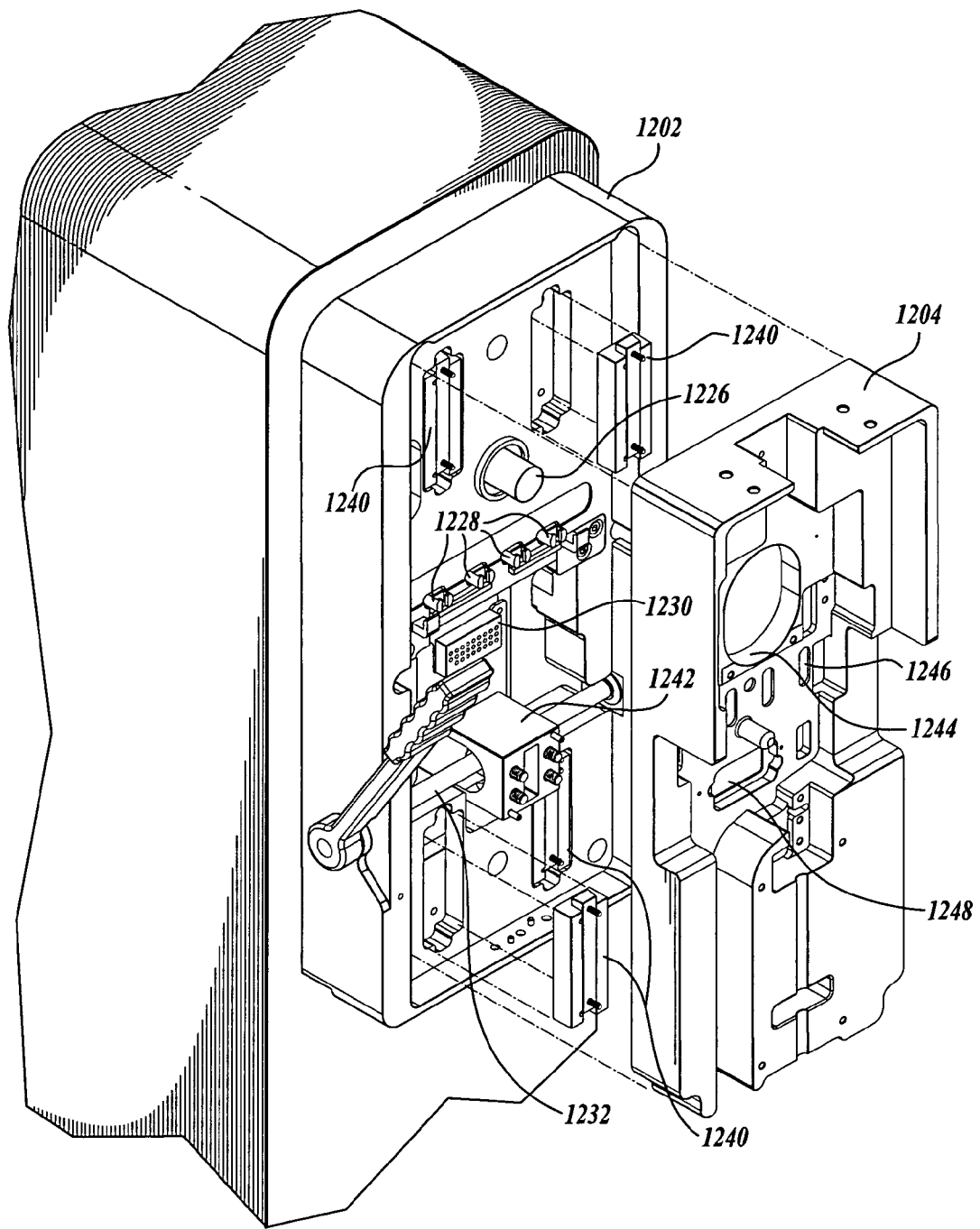
FIG. 18 and FIG. 19 are corresponding fragmentary top perspectives of the console showing some parts in exploded relationship in each instance.

FIG. 18 shows parts of the sliding plate 1204 broken away from the interface plate 1202. The sliding plate connects to the interface plate by linear bearings 1240 which include slide blocks secured to the sliding plate and vertical channels secured to the interface plate. A follower 1242 fits over the cam of shaft 1232 and is secured to the rear of the sliding plate 1204. The sliding plate has a vertically elongated opening 1244 for the pump shaft 1226 and vertically elongated openings 1246 for the end effectors 1228. The console electrical connector 1230 is carried by the sliding plate and projectors through a hole 1248.

Figure 19:
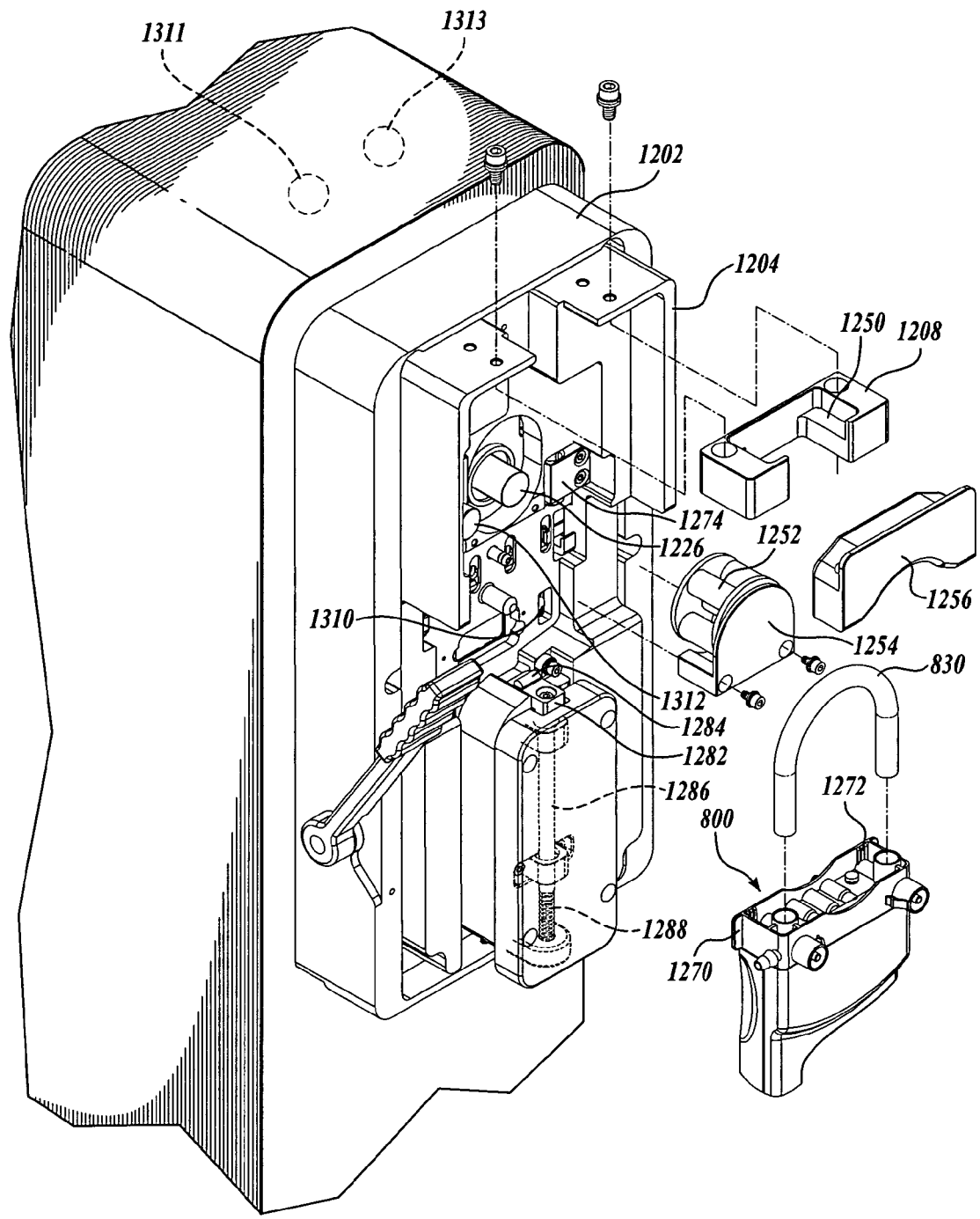

FIG. 19 shows most of the components of the sliding plate 1204 connected to the interface plate 1202. The reservoir mount 1208 connects to the sliding plate at the top and has a stepped opening 1250 that the cap of the reservoir fits in. The pump wheel 1252 is keyed to the pump shaft 1226. A guard plate 1254 covers the outer end and bottom part of the pump wheel 1252. The pump wheel cooperates with an occlusion plate 1256 which is secured to the sliding plate above the pump wheel. When the sliding plate is lowered, the occlusion plate holds the tube 830 of the proximal connector 800 in working relationship with the pump wheel.

Figure 20:
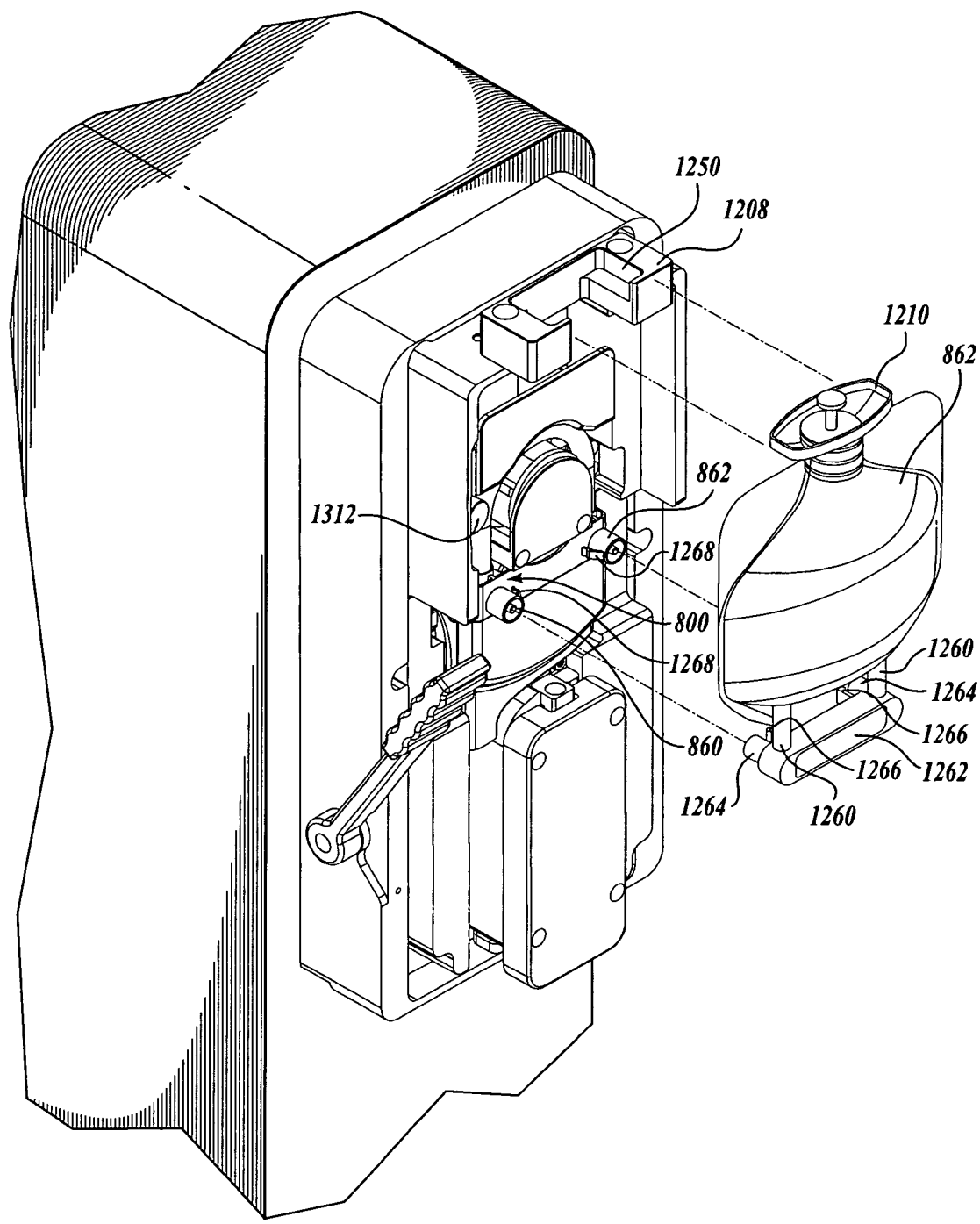
FIG. 20 is a corresponding fragmentary top perspective of the console showing most parts assembled, but with a fluid reservoir detached.
Figure 21:
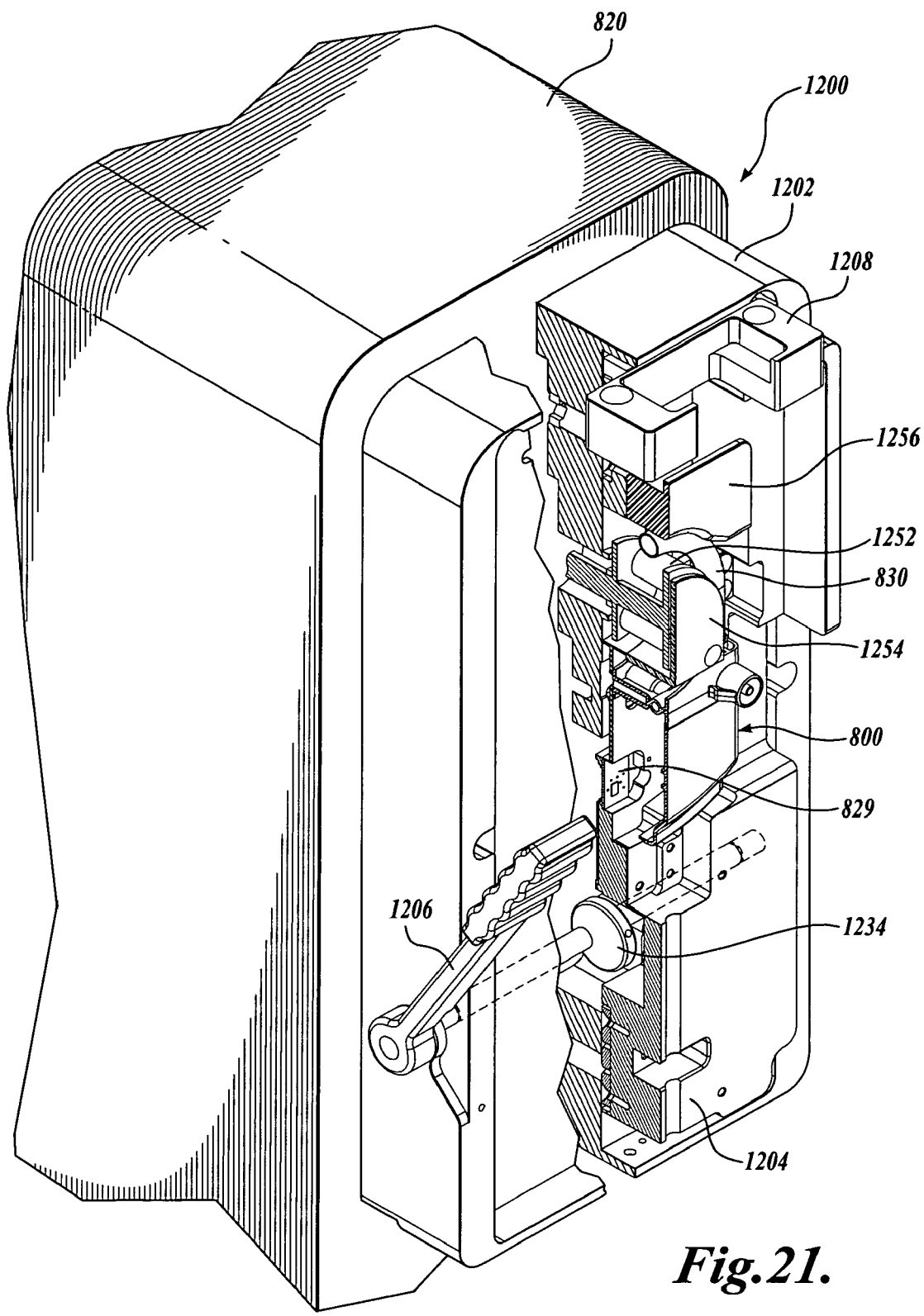
FIG. 21 is a top perspective of the console with parts broken away.

With reference to FIG. 20, showing the parts assembled except for the reservoir 810, the cap 1210 of the reservoir is rigid or substantially rigid and sized to fit in the stepped opening 1250 of the mount 1208. The central bag of the reservoir can be flexible, with bottom fittings 1260 that mate with corresponding fittings of a rigid horizontal connector 1262. Connector 1262 has rear ports 1264 that fit snugly in the ports 860, 862 of the proximal connector 800. Latch fingers 1266 adjacent to the ports 1264 interfit with the detents 1268 adjacent to the ports 860, 862 for reliably maintaining a fluid-tight connection between the reservoir and the manifold piece of the proximal connector 800. It should be noted that the reservoir can be connected to the sliding plate and proximal connector, and detached therefrom, with one hand. During assembly, the reservoir is hung from the mount 1208 by its cap 1210, followed by pressing the horizontal connector 1262 inward until the firm snap fit of the latch fingers 1266 in the detents 1268 is detected. Similarly, only one hand is required to detach or change the reservoir, by pulling outward on the connector 1262 sufficiently to release the detents, followed by lifting the cap 1210 from the mount 1208.

Similarly, the proximal connector itself can be secured to the sliding plate 1204 with one hand. Adjustable detents can be provided to reliably hold the proximal connector in position against the sliding plate, but not so tight that they cannot be overcome with one hand when the operating lever is in its up position. Preferably, spring loaded detents are provided toward the top and bottom of the proximal connector where it fits in the sliding plate 1204.

With reference to FIG. 19, in one embodiment the top manifold piece of the proximal connector 800 has thin tabs or wings 1270 at opposite sides, and closely adjacent ribs 1272 in recessed portions or sockets inward of the tabs. Still referring to FIG. 19, spring loaded detents 1274 are provided at each side of the sliding plate, only one such detent being shown in FIG. 19. The general construction of each detent is shown in more detail in FIG. 27. Each detent 1274 has a spring loaded ball 1276 positioned to overlie the detent ribs 1272 on the proximal connector 800. The force required to push the upper portion of the proximal connector into position can be adjusted (e.g., lessened from the position shown in FIG. 27) by mounting the spring loaded ball in an externally threaded stud 1280 which itself is threaded within a sleeve 1282 secured to the sliding plate.

Figure 24:
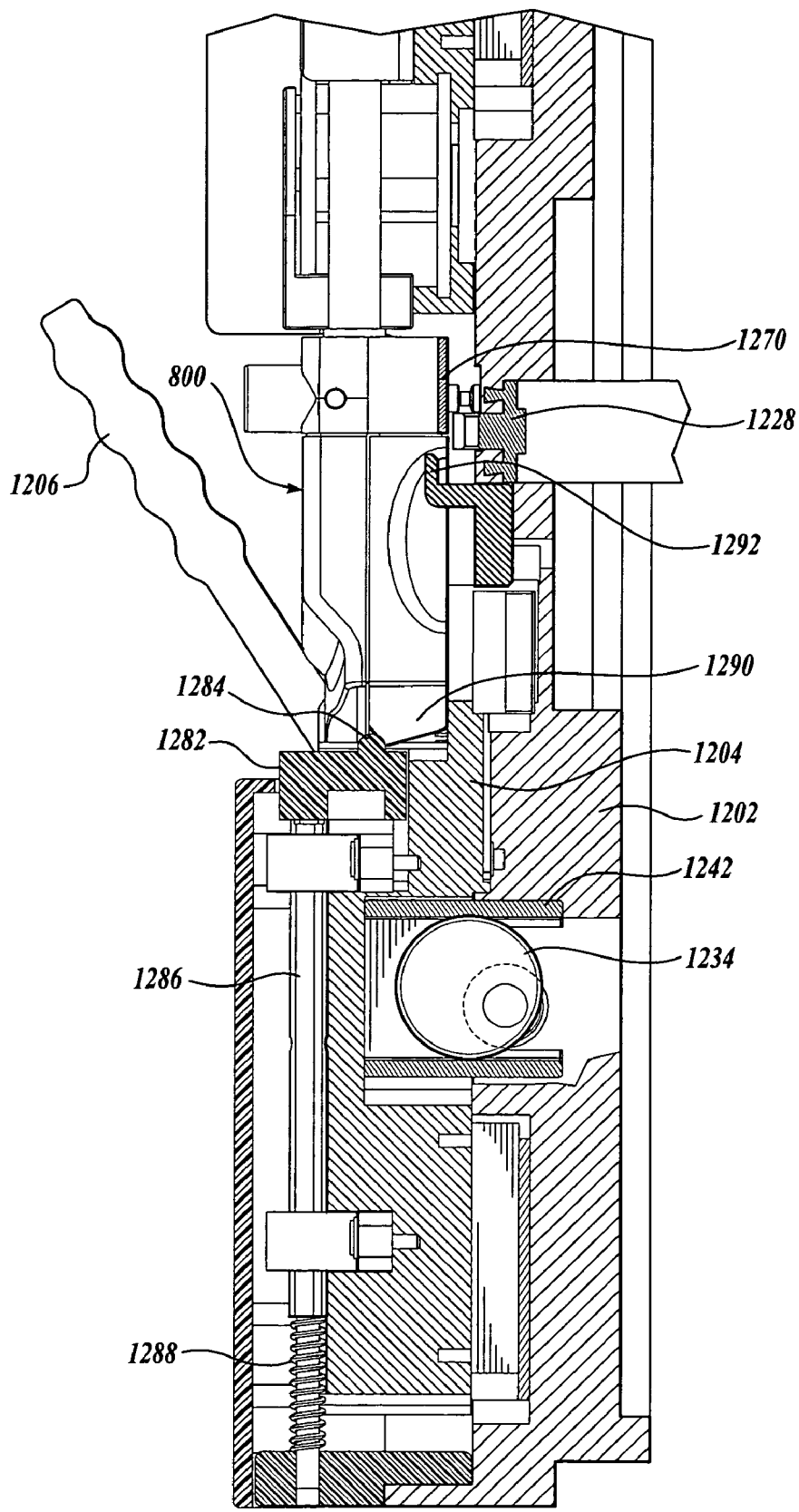
FIG. 24 and FIG. 25 are corresponding diagrammatic, vertical sections showing parts in different positions.
Figure 25:
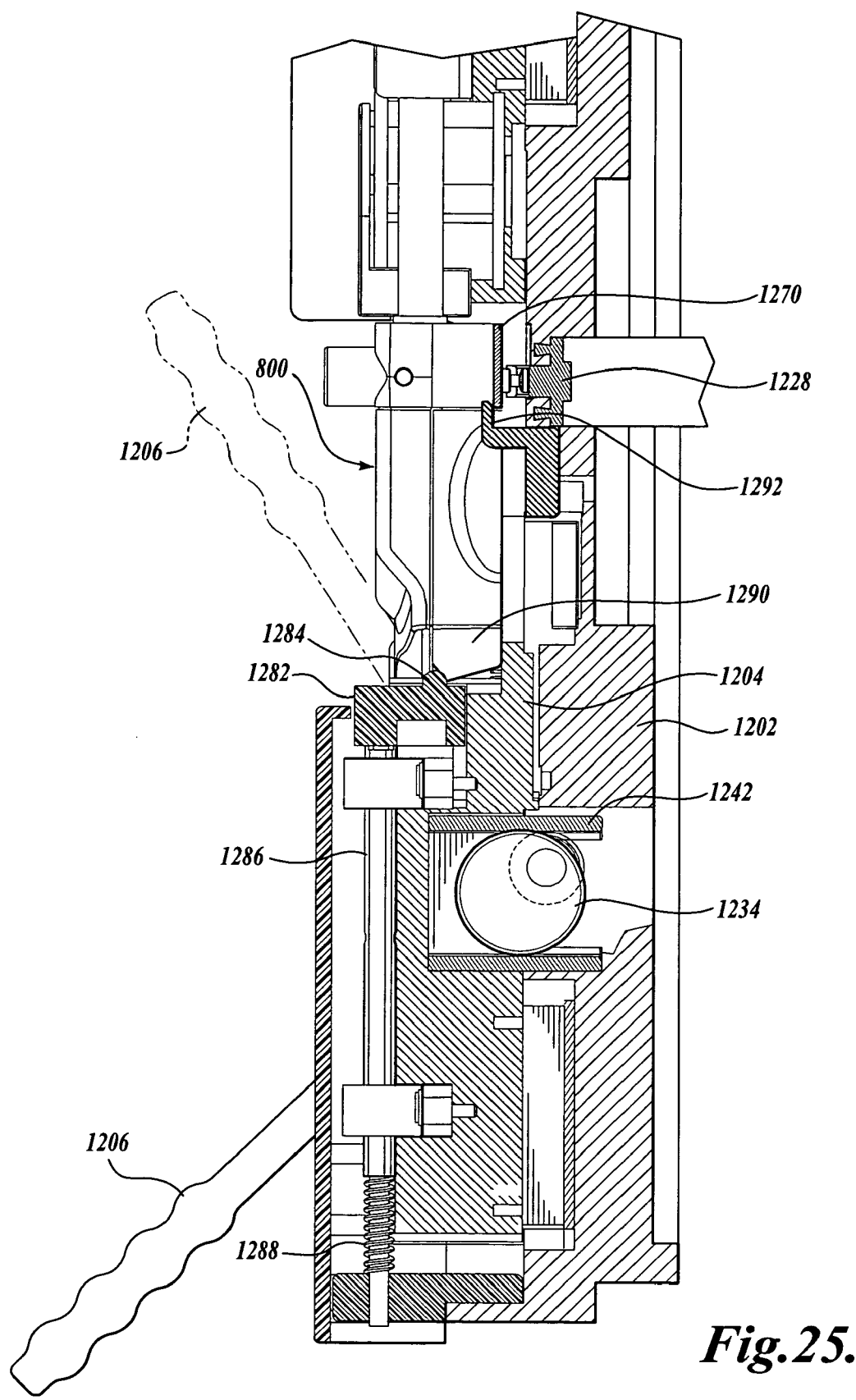
Figure 26:
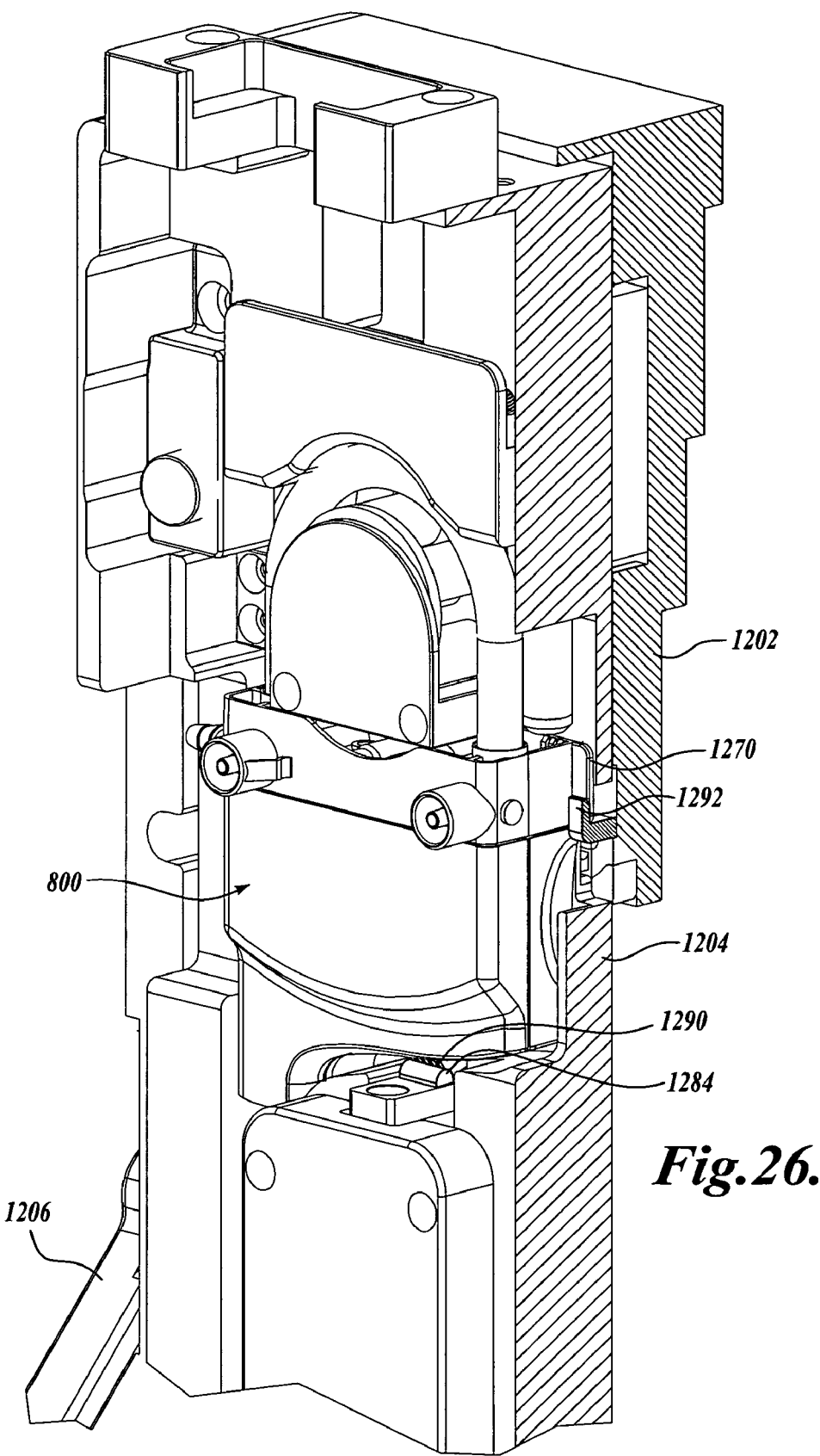
FIG. 26 is a diagrammatic, top perspective showing detents on console-mounted interface units for the proximal connector.
Figure 27:
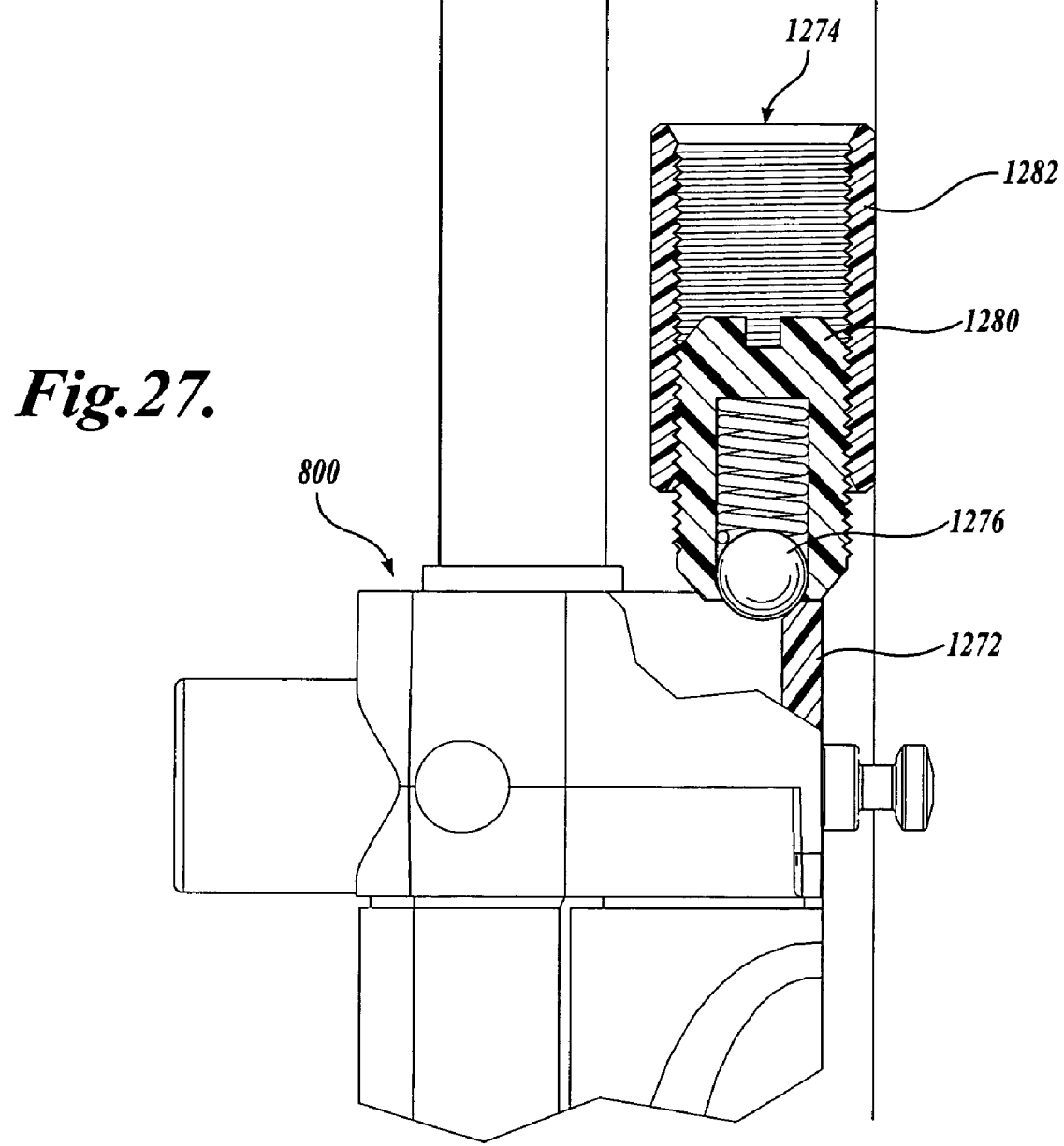
FIG. 27 is an enlarged, diagrammatic detail of part of the detent mechanism for the proximal connector.

Another spring loaded detent is provided toward the bottom portion of the proximal connector. FIG. 19 shows the detent plate 1282 with a transverse projection 1284. Plate 1282 and its projection 1284 are carried on a spring loaded rod 1286 biased upward by the bottom spring 1288. This construction is also seen in, for example, FIG. 24. The corresponding detent piece on the proximal connector can be seen in various views, including, for example, FIGS. 10A and 10C where it is labeled 1290. Detent piece 1290 has opposite sloping surfaces which cooperate with the projection 1284 by wedging it downward, against the biasing force of spring 1288, as the proximal connector is inserted. FIG. 24 shows the position after the proximal connector 800 has been inserted into the sliding plate and the front angled or ramped portion of the detent piece 1290 fits behind the projection 1284. From this position, preferably after connection of the reservoir, the operating handle 1206 can be swung downward to the position shown in FIG. 25. The cam 1234 cooperates with the follower to move the slide plate 1204 downward and compress the bottom spring 1288. At the same time, the wings 1270 toward the top of the proximal connector fit behind stationary hooks 1292 carried by the interface plate 1202 (see also FIG. 26). Substantially greater force holds the projection 1284 up behind the recess formed by the back of the ramp 1290 when the lever 1206 has been swung down to the position of FIG. 25 than when it is in its up position with the spring 1208 less compressed as shown in FIG. 24. As the plate shifts downward, the valve spool ends or caps fit into the effectors 1228. Preferably, the electrical connection is made when the proximal connector is first attached (lever raised) and is maintained as the sliding plate is lowered. For example, the electrical connector 1230 of the console can include spring-loaded pins ("pogo pins") that mate with corresponding contacts on the electrical board 829 of the proximal connector. Alternatively, a different electrical connection could be used such that the electrical contacts on the separate parts are connected as the sliding plate moves down to the operating position.

Figure 22:
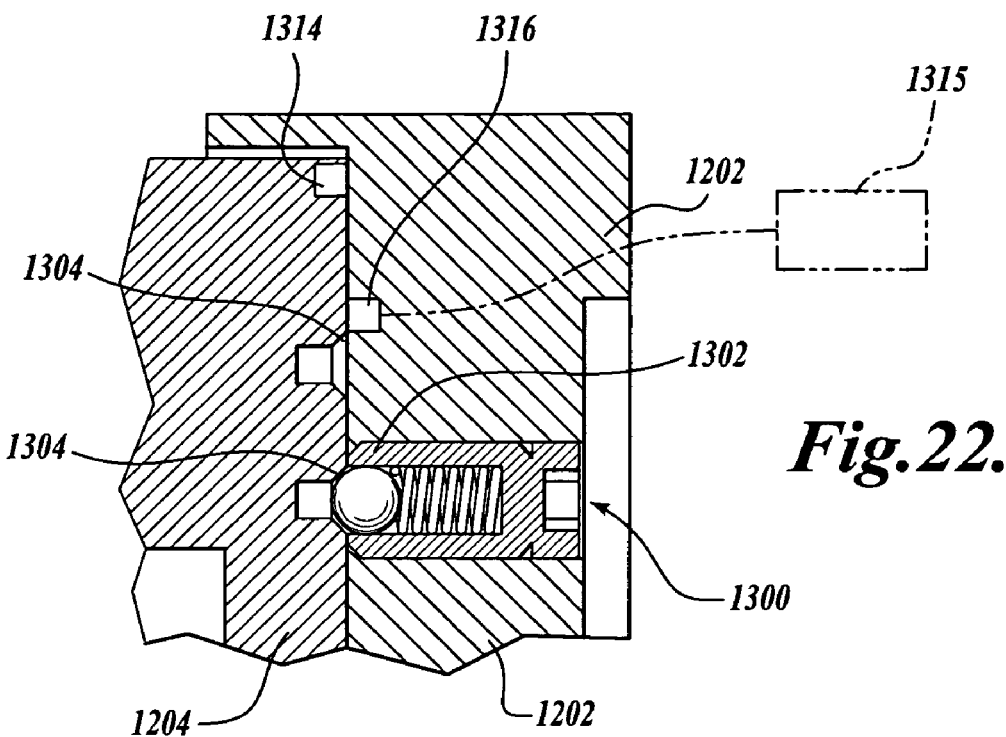
FIG. 22 and FIG. 23 are enlarged detail vertical sections illustrating detents for relatively moveable parts of the console.
Figure 23:
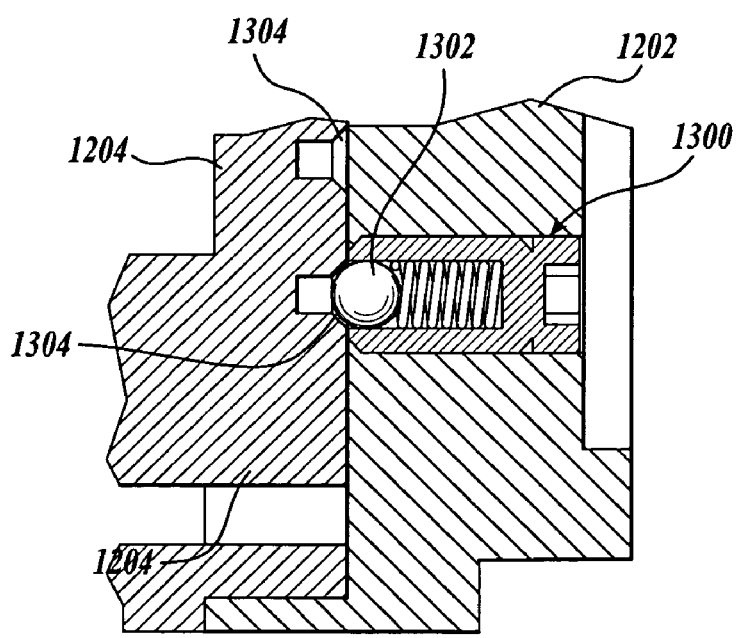

Additional precautions can be provided to assure that a secure and correct connection is made between the proximal connector and the console. FIGS. 22 and 23 show detent mechanism 1300 providing tactile feedback for the operator when the lever is in the full up or full down position. The interface plate 1202 carries spring-loaded balls 1302 which fit in tapered recesses 1304 of the sliding plate 1204 when the sliding plate is in the full up or full down position. It also is preferred that sensors and indicators be provided so that the operator can easily distinguish whether or not proper connections have been made. With reference to FIG. 19, an optical sensor 1310 can be mounted on the interface plate 1202 in line with an opening of the sliding plate, to detect when the proximal connector 800 has been seated in the sliding plate. An operator may detect this by an indicator on the graphical user interface, represented diagrammatically at 1311 in FIG. 19. As seen in FIGS. 19 and 20, a capacitive sensor 1312 can be provided adjacent to the pump wheel to detect the presence of the reservoir 810 if filled with liquid to a height at least as high as the capacitive sensor. A corresponding indicator 1313 (FIG. 19) can be provided on the graphical user interface. In a representative embodiment, the reservoir may hold 500 ml of liquid, and the capacitive sensor may detect when the liquid bevel has fallen below 200 ml or so. With reference to FIG. 22, another sensing mechanism can detect the position of the sliding plate 1204 relative to the stationary interface plate 1202. In the illustrated embodiment, a small magnet 1314 is carried on the rear of the sliding plate, in line with a Hall effect sensor 1316 carried on the stationary plate. An indicator 1315 can be provided on the graphical user interface so that the operator can easily tell when the sliding plate has been moved down to the operating position in which the magnet will overly the Hall effect sensor.

As will be appreciated by those of ordinary skill in the art, the present invention is not limited to the configurations of endoscopic systems as described and shown in reference to FIGS. 1 through 27. For example, the present invention may be used with an endoscope that is steered by actuators in the console in response to commands received from a user input device such as a joystick or other mechanism. Furthermore, the manifold in the connector 800 may also be used to deliver liquid from alternate fluid sources either in the proximal connector or the endoscope such as is shown in FIGS. 1 and 6.

While illustrative embodiments have been illustrated and described, it will be appreciated that various changes can be made therein without departing from the spirit and scope of the invention.

The invention claimed is:

1. An interface between an endoscope shaft proximal end connector and a console, the console and proximal end connector having a first set of separate mating connectors that mate for control of the endoscope, the first set of separate mating connectors including a set of mating connectors of the console and a set of mating connectors of the proximal end connector, said interface comprising:
  a lever mounted on the console moveable between a first position and a second position;
  a cam rotated by the lever;
  a sliding plate mounted on the console adjacent to the set of mating connectors of the console, including a cam follower that engages the cam; the sliding plate being moveable relative to the console between a receiving position when the lever is in the first position and an operating position when the lever is in the second position, the sliding plate being adapted to receive the proximal end connector of the endoscope shaft when the lever is in the first position such that the set of mating connectors of the console and the set of mating connectors of the proximal end connector are in a non-mating relationship and to engage the set of mating connectors of the proximal end connector and the set of mating connectors of the console in a mating relationship when the lever is moved to the second position.

2. The interface defined in claim 1, in which the endoscope proximal end connector and sliding plate are constructed and arranged for manual attachment of the proximal end connector to the sliding plate when the sliding plate is in the receiving position, and at least one detent for normally retaining the proximal end connector attached to the sliding plate.

3. The interface defined in claim 2, in which the detent applies a first force resisting separation of the proximal end connector and the sliding plate when the lever is in the first position and a second force, stronger than the first force, when the lever is in the second position.

4. The interface defined in claim 2, in which the detent includes a spring loaded projection on one of the sliding plate and the proximal end connector and a corresponding recess or socket on the other for receiving the projection and resisting separation of the two based on the force of the spring.

5. The interface defined in claim 4, in which the sliding plate and proximal end connector are constructed and arranged relatively such that the force retaining the proximal end connector attached to the sliding plate is greater when the lever is in the second position than when the lever is in the first position.

6. The interface defined in claim 1, in which the sliding plate is slidable linearly relative to the console between the receiving and operating positions.

7. The interface defined in claim 1, in which the set of mating connectors of the proximal end connector include a plurality of valves moveable between open and closed positions to regulate flow of fluid therethrough, and the set of mating connectors of the console include a plurality of actuators for moving the valves, the valves and actuators having respective portions that interfit when the proximal end connector is attached to the sliding plate and the lever is in the second position, but which respective portions do not operably interfit when the lever is in the first position.

8. The interface defined in claim 7, including a fluid reservoir manually attachable to and detachable from the proximal end connector, the proximal end connector having a manifold for supplying liquid from the reservoir to one or more of the valves.

9. The interface defined in claim 1, in which the console and proximal end connector include a second set of separate mating connectors that mate for control of the endoscope, the mating connectors of the second set being operably connected when the proximal end connector is received in the sliding plate and the lever is in the first position as well as when the lever is in the second position.

10. The interface defined in claim 9, in which the second set of connectors are electrical connectors.

\* \* \* \* \*

UNITED STATES PATENT AND TRADEMARK OFFICE
CERTIFICATE OF CORRECTION

| | | |
|---|---|---|
| PATENT NO. | : 7,597,662 B2 | Page 1 of 1 |
| APPLICATION NO. | : 11/430518 | |
| DATED | : October 6, 2009 | |
| INVENTOR(S) | : Litscher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this

Twenty-eighth Day of September, 2010

David J. Kappos
*Director of the United States Patent and Trademark Office*